(12) United States Patent
Kiderman et al.

(10) Patent No.: US 9,247,870 B2
(45) Date of Patent: Feb. 2, 2016

(54) METHOD AND APPARATUS FOR SYSTEM SYNCHRONIZATION IN VIDEO OCULOGRAPHY BASED NEURO-OTOLOGIC TESTING AND EVALUATION

(71) Applicant: Neuro Kinetics, Inc., Pittsburgh, PA (US)

(72) Inventors: Alexander D Kiderman, Pittsburgh, PA (US); Ian Shirey, Pittsburgh, PA (US); Daniel Sweeney, Pittsburgh, PA (US)

(73) Assignee: NEURO KINETICS, INC., Pittsburgh, PA (US)

( * ) Notice: Subject to any disclaimer, the term of this patent is extended or adjusted under 35 U.S.C. 154(b) by 129 days.

(21) Appl. No.: 14/216,981

(22) Filed: Mar. 17, 2014

(65) Prior Publication Data

US 2014/0320808 A1    Oct. 30, 2014

Related U.S. Application Data

(60) Provisional application No. 61/918,243, filed on Dec. 19, 2013, provisional application No. 61/799,959, filed on Mar. 15, 2013.

(51) Int. Cl.

| | |
|---|---|
| *A61B 3/14* | (2006.01) |
| *A61B 3/00* | (2006.01) |
| *A61B 3/11* | (2006.01) |
| *A61B 3/113* | (2006.01) |
| *A61B 3/02* | (2006.01) |

(52) U.S. Cl.
CPC .................. *A61B 3/0091* (2013.01); *A61B 3/02* (2013.01); *A61B 3/11* (2013.01); *A61B 3/112* (2013.01); *A61B 3/113* (2013.01); *A61B 3/145* (2013.01)

(58) Field of Classification Search
USPC .................................................. 351/200–246
See application file for complete search history.

(56) References Cited

U.S. PATENT DOCUMENTS

| | | | | |
|---|---|---|---|---|
| 7,261,415 | B2 * | 8/2007 | Chernyak ............. | A61B 1/1015 351/209 |
| 7,431,457 | B2 * | 10/2008 | Chernyak ............. | A61B 3/1015 351/205 |
| 7,448,751 | B2 | 11/2008 | Kiderman et al. | |
| 7,520,614 | B2 | 4/2009 | Joos et al. | |
| 7,651,224 | B2 | 1/2010 | Wood et al. | |
| 7,665,845 | B2 | 2/2010 | Kiderman et al. | |
| 7,731,360 | B2 | 6/2010 | MacDougall et al. | |
| 7,753,523 | B2 | 7/2010 | Kiderman et al. | |
| 7,866,818 | B2 | 1/2011 | Schroeder et al. | |

(Continued)

*Primary Examiner* — Mohammed Hasan
(74) *Attorney, Agent, or Firm* — Blynn L. Shideler; Krisanne Shideler; BLK Law Group

(57) ABSTRACT

A video oculography based neuro-otologic testing and evaluation apparatus and associated method comprises the steps of: Obtaining images of the subject's eyes with a digital camera; Selectively displaying visual stimulus to the subject on a display; Generating each visual stimulus to be displayed from a controller; Receiving and storing data signals from each digital camera in the controller; Calculating eye related data from the digital camera images and visual stimulus; Displaying the eye related data to users; Generating a video synchronization signal by the controller associated with each visual stimulus which identifies when the display is displaying the associated visual stimulus; Receiving and coupling the video synchronization signal with at least the eye data from the digital camera; and Synchronizing calculations based upon the eye data and the visual stimulus by the controller.

20 Claims, 15 Drawing Sheets

(56) References Cited

U.S. PATENT DOCUMENTS

| | | |
|---|---|---|
| 8,333,472 B2 | 12/2012 | Kiderman |
| 8,585,609 B2 | 11/2013 | Kiderman et al. |
| 2005/0099601 A1 * | 5/2005 | MacDougall ........ A61B 3/113 351/209 |
| 2007/0132841 A1 | 6/2007 | MacDougall et al. |
| 2007/0177103 A1 | 8/2007 | Migliaccio et al. |
| 2008/0049186 A1 | 2/2008 | MacDougall et al. |
| 2008/0049187 A1 | 2/2008 | Joos et al. |
| 2012/0081666 A1 | 4/2012 | Kiderman et al. |

* cited by examiner

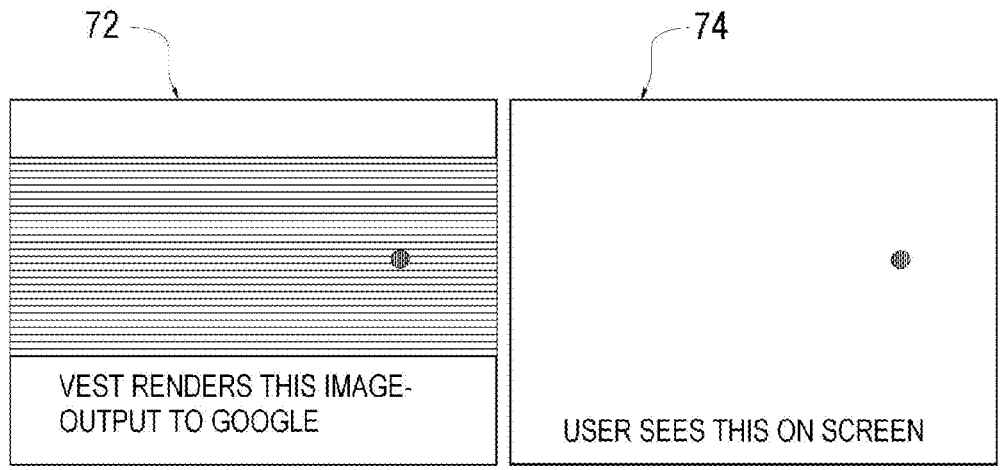
FIG. 10A  FIG. 10B
FIG. 4B
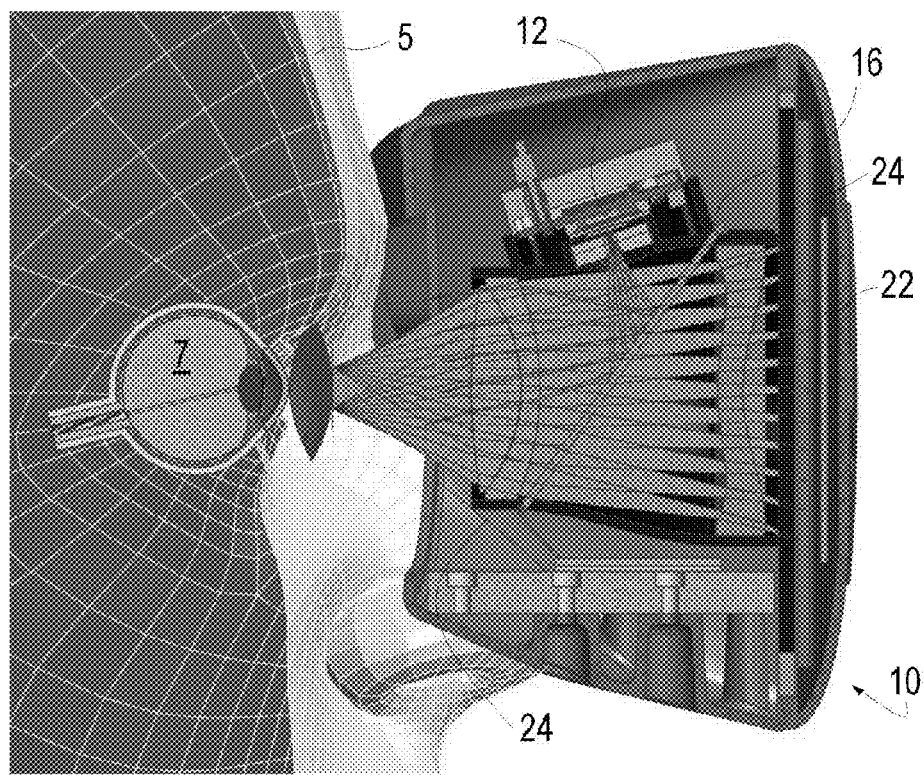

FIG. 12C

| RESULTS | | |
|---|---|---|
| | LEFT EYE | RIGHT EYE |
| LATENCY (SEC) | 0.15 | 0.16 |
| DURATION (SEC) | 0.04 | 0.04 |
| AMPLITUDE (SEC) | 7.53 | 9.73 |
| MAX VEL (DEG/SEC) | 255.83 | 370.87 |
| ACCURACY (%) | 75.92 | 98.10 |
| FINAL ACCURACY (%) | 75.92 | 98.10 |
| | LEFT BUTTON | RIGHT BUTTON |
| LATENCY (SEC) | NaN | 0.57 |
| ERROR | WRONG BUTTON PRESS | |

METHOD AND APPARATUS FOR SYSTEM SYNCHRONIZATION IN VIDEO OCULOGRAPHY BASED NEURO-OTOLOGIC TESTING AND EVALUATION

RELATED APPLICATIONS

The present application claims the benefit of U.S. provisional application Ser. No. 61/799,959 entitled "Method and Apparatus for Objective Ophthalmic Eye Testing in Video-Oculography Applications" filed Mar. 15, 2013.

The present application claims the benefit of U.S. provisional application Ser. No. 61/918,243 entitled "High Speed VOG Synchronization For Head Mounted VOG System With Onboard Display And Compact Integrated Optics And Hot Mirror Unit" filed Dec. 19, 2013.

BACKGROUND OF THE INVENTION

1. Field of the Invention

The present invention relates to system synchronization in video oculography based neuro-otologic testing and evaluation.

2. Background Information

A standard ophthalmic exam is a series of tests done to check a subject's vision and the health of the subject's eyes. Included in this testing are standard tests used to check visual acuity, pupil function, eye movement and peripheral vision. The basic format or operation of these tests are well known to the practitioners the field, some general (overlapping) categories used in the field to broadly describe such testing includes eye movement tests, visual acuity tests, Pupillometry tests, nystagmus tests, smooth pursuit tests, saccades tests, optokinetic tests, peripheral vision testing, subjective visual horizontal and subjective visual vertical tests.

Visual acuity tests may be performed in many different ways. It is a quick way to detect vision problems and is frequently used in schools or for other mass screening, e.g. military recruits. Driver license bureaus often use a small device that can test the eyes both together and individually.

Pupillometry tests represent conventional examination of pupillary function includes inspecting the pupils for equal size (1 mm or less of difference may be normal), regular shape, reactivity to light, and direct and consensual accommodation. A swinging flashlight test is one known pupillometry test which may also be desirable if neurologic damage is suspected. In a normal reaction to the swinging-flashlight test, both pupils constrict when one is exposed to light. As the light is being moved from one eye to another, both eyes begin to dilate, but constrict again when light has reached the other eye.

Eye movement testing can also be called extra-ocular muscle function testing is an examination of the function of the eye muscles. These tests observe the movement of the eyes in six specific directions.

Peripheral vision testing is also called visual field testing. It has been suggested that evaluation of the visual fields should never be omitted from the basic eye examination. Testing the visual fields consists of confrontation field testing in which each eye is tested separately to assess the extent of the peripheral field.

In many of the above testing, namely check visual acuity, pupil function, eye movement and peripheral vision, testing apparatus have been developed to automatically supply the appropriate visual stimulus to the subject to conduct the test. Further, these devices can be found in desk mounted arrangements which accommodate the subjects head, wall or desk mounted units (e.g. monitors) that provide that the subject is a fixed distance away typically in a chair, chair mounted projection type units mounted on the subjects chair that project onto the wall, and even head mounted units attached to the subject.

Within the meaning of this application any ophthalmic eye testing device that supplies a predetermined visual stimulus to the subject in a predetermined location (which may move) is an automated ophthalmic eye testing device. One such automated ophthalmic eye testing device is the laser based PURSUIT TRACKER® system of visual stimulus generator available from the applicant, Neuro-Kinetics, Inc. This type of device, and some of the testing that can be performed with such devices, is described in U.S. Pat. Nos. 7,651,224 and 8,333,472 which are incorporated herein by reference. Additionally the ophthalmic eye testing device may be incorporated with an eye tracker such as described in U.S. Pat. No. 8,585,609 which is incorporated herein by reference.

Eye trackers measure eye movement, i.e. rotations of the eye, in one of several ways, but principally they fall into three categories:

One category of eye tracker uses an attachment to the eye, such as a special contact lens with an embedded mirror or magnetic field sensor, and the movement of the attachment is measured with the assumption that it does not slip significantly as the eye rotates. Measurements with tight fitting contact lenses have provided extremely sensitive recordings of eye movement, and magnetic search coils are the method of choice for researchers studying the dynamics and underlying physiology of eye movement.

A second category of eye tracker uses electric potentials measured with electrodes placed around the eyes. The eyes are the origin of a steady electric potential field, which can also be detected in total darkness and if the eyes are closed. It can be modeled to be generated by a dipole with its positive pole at the cornea and its negative pole at the retina. The electric signal that can be derived using two pairs of contact electrodes placed on the skin around one eye is called Electrooculogram (EOG). If the eyes move from the center position towards the periphery, the retina approaches one electrode while the cornea approaches the opposing one. This change in the orientation of the dipole and consequently the electric potential field results in a change in the measured EOG signal. Inversely, by analyzing these changes in eye movement can be tracked. Due to what is known as the discretization given by the common electrode setup two separate movement components—a horizontal and a vertical—can be identified. The potential difference is not constant and its variations make it challenging to use EOG for measuring slow eye movement and detecting gaze direction. EOG is, however, a very robust technique for measuring saccadic eye movement associated with gaze shifts and detecting blinks. It is a very light-weight approach that, in contrast to current video-based eye trackers, only requires very low computational power, works under different lighting conditions and can be implemented as an embedded, self-contained wearable system. It is thus the method of choice for measuring eye movement in mobile daily-life situations and REM (Rapid Eye Movement) phases during sleep.

The third broad category of eye tracker, which is the category relevant to the present invention, uses some non-contact, optical method for measuring eye motion. Generally these are video based eye trackers. Light, typically infrared, is reflected from the eye and sensed by a video camera or some other specially designed optical sensor. The information is then analyzed to extract eye rotation from changes in reflections. One class of video based eye trackers typically uses the corneal reflection (the first Purkinje image) and the center of the pupil as features to track over time. A more sensitive type of eye tracker, the dual-Purkinje eye tracker, uses reflections from the front of the cornea (first Purkinje image) and the back of the lens (fourth Purkinje image) as features to track. A still more sensitive method of tracking in this class is to image features from inside the eye, such as the retinal blood vessels, and follow these features as the eye rotates. Other video systems digitize the eye and locate the pupil in the image and utilize object recognition analysis or processing to locate and track the pupil in the digitized image. Optical methods, particularly those based on video recording, are widely used for gaze tracking and are favored for being non-invasive and inexpensive.

With this general background, the problems addressed by the present claimed invention can be described. Many of the ophthalmic test parameters represent physiologic parameters only obtainable with a high speed devices, and thus only became possible in VOG systems with cost effective high speed cameras. These parameters, and other "high speed parameters" such as second order or higher corrective saccadic eye movements described in U.S. Patent Publication 2012-0081666 which is incorporated herein by reference, and micro-saccades (defined or described as involuntary saccades produced during attempted fixation. see the CALTECH article "Microsaccades: a Neurophysiological; Analysis" by Susana Martinez-Conde of the Barrow Neurological Institute, Trends in Neurscience Volume 32 No. 9, Pgs 463-475, 2009.), Drifts (described as "slow curvy motions between microsaccades), Tremors (described as very fast (about 90 Hz) small oscillations superimposed upon drifts) etc, raise a new issue with such video based systems, namely the synchronization of the actual timing of the visual stimulus with measurements associated with that timing.

Basically measurement of these high speed parameters in a video based eye tracking system can become inaccurate due to the processing delays within the conventional computer without a synchronization system. There is a need in the art, system synchronization in video oculography based neuro-otologic testing and evaluation.

SUMMARY OF THE INVENTION

One aspect of the present invention provides a video oculography based neuro-otologic testing and evaluation method which comprises the steps of: Obtaining images of at least one of the subject's eyes at least at 60 frames per second with at least one digital camera attached to a base positioned adjacent to a subject's head; Selectively displaying visual stimulus to the subject on a display visible to the subject; Generating each visual stimulus to be displayed from a controller coupled to the display; Receiving and storing data signals from each digital camera in the controller; Calculating eye related data from the digital camera images and the visual stimulus; Displaying the eye related data to users; Generating a video synchronization signal by the controller associated with each visual stimulus which identifies when the display is displaying the associated visual stimulus to the subject; Receiving and coupling the video synchronization signal with at least the eye data from the digital camera; and Synchronizing calculations based upon the eye data and the visual stimulus by the controller based upon the received video synchronization signal and the eye data from the digital camera.

Another aspect of the present invention provides a video oculography based neuro-otologic testing and evaluation system comprising: a base adapted to be positioned adjacent to a subject's head; at least one digital camera attached to the base, operating at least at 60 frames per second and configured to take images of at least one of the subject's eyes; a display for selectively displaying visual stimulus to the subject; a controller coupled to the display generating each visual stimulus to be displayed and coupled to each digital camera and receiving and storing data signals there from, the controller configured to calculate eye related data from the digital camera images, and configured to display the eye related data to users; a video synchronization signal generated by the controller associated with each visual stimulus which identifies when the display is displaying the associated visual stimulus to the subject; receiving and coupling the video synchronization signal with at least the eye data from the digital camera, wherein the received video synchronization signal and the eye data from the digital camera are utilized by the controller to synchronize calculations based upon the eye data and the visual stimulus.

These and other advantages of the present invention will be described in connection with the preferred embodiments that are disclosed in connection with attached figures wherein like reference numerals represent like elements throughout.

BRIEF DESCRIPTION OF THE FIGURES

FIGS. 10A-B schematically illustrates a video synchronization signal for use with the system according to one embodiment of the present invention;

FIGS. 12A-F illustrate display results and control parameters associated with the saccade reaction time testing protocol according to one embodiment of the present invention;

FIGS. 13A-B illustrate display results and control parameters associated with an objective anti-saccade test response testing protocol according to one embodiment of the present invention;

DESCRIPTION OF THE PREFERRED EMBODIMENTS

Figure 1:
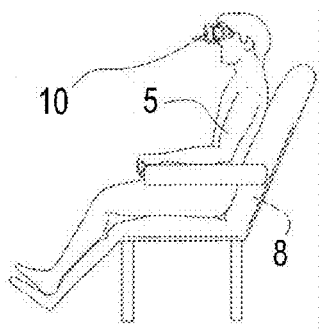
FIG. 1 is a schematic view of a subject wearing a head mounted video oculography system (VOG) system in accordance with one aspect of the present invention.

The most widely used current eye tracker designs are video-based eye trackers. Video-based eye trackers within the meaning of this application are those systems obtaining visual images of the eyes. Some of these eye trackers have a convergence or gaze tracking function to calculate where the subject is looking. This calculated gaze may, for example, may be used as an input or control mechanism for other actions (e.g., such as proposed in certain heads up display (HUD) control systems. The record of the eye tracking has also been used to evaluate advertizing materials and the like. More relevant to the present invention, the record of the eye tracking has also been analyzed for eye evaluation purposes, which is generally the subject of the present invention. Video-based eye trackers are also known as Video-OculoGraphy (VOG) systems where the data obtained is used to analyze the subject's eyes and other physical attributes, as eye data has proven to be reliable biomarkers for various neurological conditions in addition to eye disorders (such as optical deficiencies in general, Oculomotor nerve palsy, Horner's syndrome, Blepharospasm, Ischemic optic neuropathy, and Glaucoma) including, but not limited to, mTBI, diabetes (diabetic retinopathy), Alzheimer's disease, Multiple Scoliosis (MS), and Parkinson syndrome. FIG. 1 is representative of a subject 5 wearing a VOG system 10 while seated in chair 8. VOG systems are now a widely used and accepted method to track and analyze eye movements, particularly for balance and neuro-otologic testing.

For example, the Applicant, Neuro Kinetics, Inc. (NKI) has produced video-oculography systems that deliver accurate, affordable, 4-dimensional eye measurement and analysis such as system 10 shown in FIG. 1. With Neuro Kinetics' I-PORTAL® brand VOG system 10 a wider range of clinicians and researchers have the opportunity to improve diagnoses and increase understanding of both the vestibular and neuro-ocular-motor systems. These types of VOG systems 10 allow the world's leading VOG researchers to view and evaluate real-time analysis of eye movement. The present application is intended to give such researchers additional objective tools for carrying their work forward.

In general in such systems 10, a camera focuses on one or both eyes and records their movement as the viewer looks at some kind of stimulus. Most modern video based eye trackers use contrast to locate the center of the pupil and use infrared and near-infrared non-collimated light to create a corneal reflection (CR). The vector between these two features can be used to compute gaze intersection with a surface after a simple calibration for an individual subject 5.

Two general types of eye tracking techniques are used in known eye trackers: Bright Pupil and Dark Pupil. Their difference is based on the location of the illumination source with respect to the optics. If the illumination is coaxial with the optical path, then the eye acts as a retro-reflector as the light reflects off the retina creating a bright pupil effect similar to red eye. If the illumination source is offset from the optical path, then the pupil appears dark because the retro-reflection from the retina is directed away from the camera. Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright. But bright pupil techniques are not effective for tracking outdoors as extraneous IR sources interfere with monitoring.

Video based eye tracker set ups vary greatly; some are head-mounted such as the system 10, some require the head to be stable (for example, with a chin rest), and some function remotely and automatically track the head during motion. Most use a sampling rate of at least 30 Hz, although this minimizes the types of data that can be obtained as such a sampling rate is too slow for reasonably obtaining higher level eye movement parameters such as corrective saccades, micro-saccades (also called micro-tremors), and some pupillary responses. Thus 50/60 Hz is most common, today while some video-based eye trackers run at 240 Hz, 350 Hz, 500 Hz or even 1000/1250 Hz, which is needed in order to capture the detail of the very rapid eye movement during eye evaluations, or during studies of neurology.

Eye movement itself is typically divided into fixations and saccades, when the eye gaze pauses in a certain position, and when it moves to another position, respectively. The resulting series of fixations and saccades is often called a scanpath. The central one or two degrees of the visual angle (the fovea) provide the bulk of visual information; the input from larger eccentricities (the periphery) is less informative. Hence, the locations of fixations along a scanpath show what information loci on the stimulus were processed during an eye tracking session. On average, fixations last for around 200 ms during the reading of linguistic text, and 350 ms during the viewing of a scene. Preparing a saccade towards a new goal takes around 200 ms.

Scanpaths are useful for analyzing cognitive intent, interest, and salience. Other biological factors (some as simple as gender) may affect the scanpath as well. Eye tracking in HCI typically investigates the scanpath for usability purposes, or as a method of input in gaze-contingent displays, also known as gaze-based interfaces.

VOG systems, such as system 10 shown in FIG. 1, often measure the rotation of the eye with respect to the measuring system. If the measuring system is a head mounted VOG system, such as system 10, then eye-in-head angles are measured. If the measuring eye tracking system is table mounted, as with scleral search coils or table mounted camera ("remote") systems, then gaze angles are measured.

In many applications, the head position is fixed using a bite bar, a forehead support or something similar, so that eye position and gaze are the same. In other cases, the head is free to move, and head movement is measured with systems such as magnetic or video based head trackers.

For head-mounted trackers, such as system 10, head position and direction are added to eye-in-head direction to determine gaze direction. For table-mounted systems, such as search coils, head direction is subtracted from gaze direction to determine eye-in-head position.

Within the meaning of this application tracking the subjects gaze with a video based eye tracker means the system is tracking where the subject's eyes are directed, typically relative to a fixation target or fixation stimulus.

A great deal of research has gone into studies of the mechanisms and dynamics of eye rotation, but the goal of eye tracking is most often to estimate gaze direction. Users may be interested in what features of an image draw the eye, for example, as advertisers have long used video based eye trackers in connection with evaluation of specific advertisements. It is important to realize that the typical eye tracker does not provide absolute gaze direction, but rather can only measure changes in gaze direction. In order to know precisely what a subject is looking at, some calibration procedure is required in which the subject looks at a point or series of points, while the eye tracker records the value that corresponds to each gaze position. (Even those techniques that track features of the retina cannot provide exact gaze direction because there is no specific anatomical feature that marks the exact point where the visual axis meets the retina, if indeed there is such a single, stable point.) An accurate and reliable calibration is essential for obtaining valid and repeatable eye movement data, and this can be a significant challenge for non-verbal subjects or those who have unstable gaze.

Each method of eye tracking has advantages and disadvantages, and the choice of an eye tracking system depends on considerations of cost and application. There is a trade-off between cost and sensitivity, with the most sensitive systems costing many tens of thousands of dollars and requiring considerable expertise to operate properly. Advances in computer and video technology have led to the development of relatively low cost systems that are useful for many applications and fairly easy to use. Interpretation of the results still requires some level of expertise, however, because a misaligned or poorly calibrated system can produce wildly erroneous data.

One difficulty in evaluating an eye tracking system is that the eye is never still, and it can be difficult to distinguish the tiny, but rapid and somewhat chaotic movement associated with fixation from noise sources in the eye tracking mechanism itself. One useful evaluation technique is to record from the two eyes simultaneously and compare the vertical rotation records. The two eyes of a normal subject are very tightly coordinated and vertical gaze directions typically agree to within +/−2 minutes of arc (RMS of vertical position difference) during steady fixation. Thus properly functioning and sensitive eye tracking system will show this level of agreement between the two eyes, and any differences much larger than this can usually be attributed to measurement error.

Objective Ophthalmic Eye Testing in Video-Oculography Applications

As noted above, the present invention also relates to Video-oculography systems 10, also called VOG systems 10. Video-oculographic recording of eye movement has been shown to be a highly effective non-invasive technology for evaluating and analyzing eye movement. See the Richard E. Gans article in the May 2001, volume 54, pages 40-42 of The Hearing Journal, which provide great insight to the beginning of practical goggle based VOG systems in 2001. Abnormalities of eye movement provide valuable information about the location of the dysfunction or disease process. Many abnormalities are specific to certain pathophysiology or pharmacologic influences. The advantage of recording/evaluating eye movements versus other axial or limb musculature is that they are easier to interpret. Eye movement is limited to movement in three planes: horizontal, vertical, and rotational. Pupillary reactions (constriction and dilation parameters) represent another category of parameters that may be desired to be tracked for certain applications.

VOG System 10 Overview

Current VOG systems 10 that accurately track eye movement for diagnostic purposes can be represented by those described in U.S. Pat. Nos. 7,448,751, 7,520,614, 7,665,845, 7,731,360, 7,753,523, and 7,866,818 and U.S. Patent Application Publications 2005-0099601, 2007-0177103, 2007-0132841, 2008-0049186, and 2008-0049187 which are incorporated herein by reference. A further example of a current state of the art VOG system include the 2013 I-Portal® brand VOG systems from Neuro-Kinetics, Inc, which is a fully digital VOG system that delivers accurate 4D eye tracking. The lightweight goggle system is offered in standard 60 Hz and 120 Hz goggle sets, both occluded and free field of view, although higher speeds of 200 Hz, 250 Hz, 340 Hz and 500 Hz and even higher are made available for particular applications. The speed of the system is determined by the cameras utilized and the higher speeds will generally increase the associated cost of the system 10.

Figure 2:
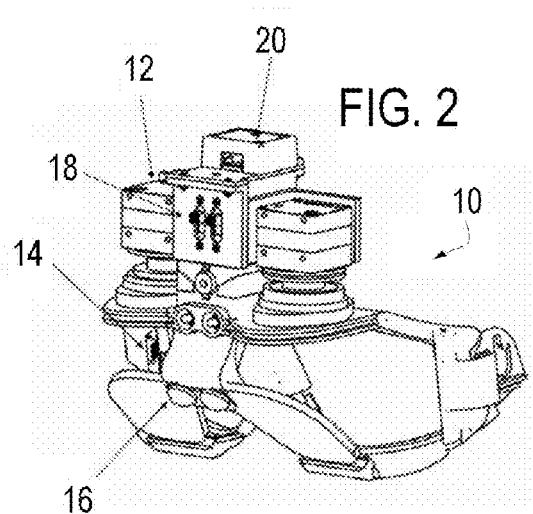
FIG. 2 is a schematic view of a head mounted open goggle based video oculography system (VOG) system in accordance with one aspect of the present invention.

The system 10 may be an open goggle VOG system such as schematically shown in FIG. 2 in which a pair of digital cameras 12 (for example, internal point firefly MV digital cameras, or XIMEA xiQ USB 25 Hz Digital Cameras, etc) are mounted in goggle frame. The eyes of the subject 5 are illuminated with infrared diodes 14 and the cameras 12 obtain images of the illuminated eyes via hot mirrors 16 (such as from Edmund Optics) directed. The system 10 includes onboard controls 14 for controlling the cameras 12 and illumination sources 14 and other items such as a calibration laser or onboard stimulus. The system 10 further includes head position sensor 18 (from CH robotics) which can supply additional physiologic position data in use. The sensor 18 is preferably a six degree of freedom sensor. The open design of system 10 of FIG. 2 allows the subject to view targets and stimulus generated on other equipment, such as a display screen or through use of a target generating system such as the PURSUIT TRACKER® system of the applicant.

Figure 3:
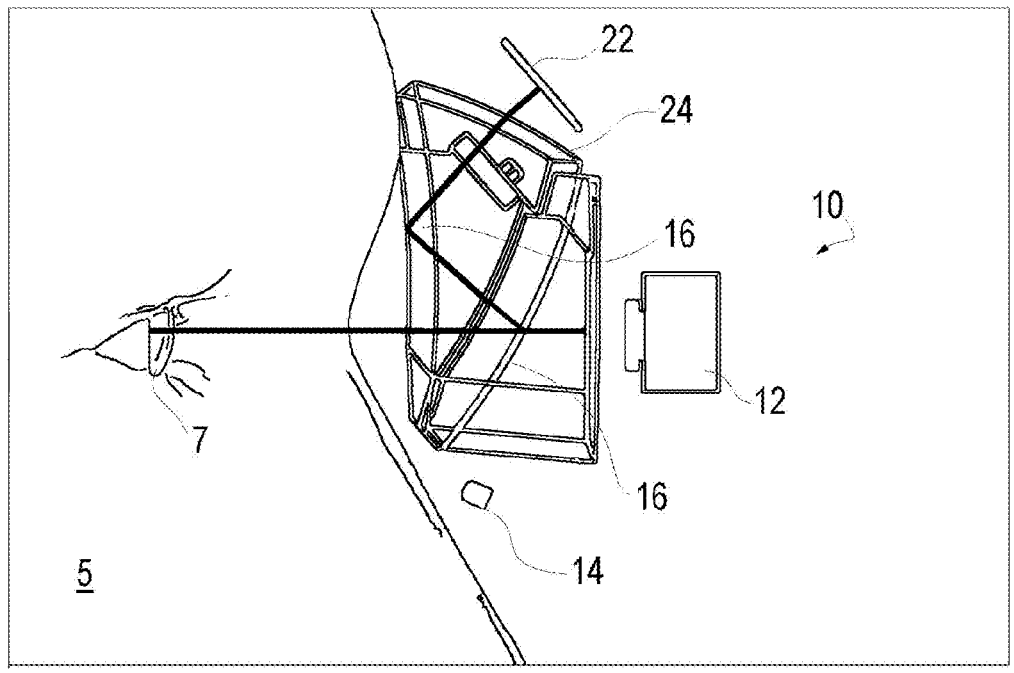
FIG. 3 is a schematic view of a head mounted closed goggle based video oculography system (VOG) system with integral stimulus screen in accordance with one aspect of the present invention.

The system 10 may be a goggle based head mounted VOG system with onboard display 22 such as schematically shown in FIG. 3. In FIG. 3 the VOG system includes an onboard display 22 that can be considered the same as a display in a cell phone of tablet computer. In this system 10 the display 22 is used to display the fixation targets and stimulus to the subject 5. The eyes 7 of the subject 5 have a view of the display 22 via hot mirrors 16 and optic 24.

Virtual reality technology will allow the display 22 to present targets and stimulus and even whole environments to the subject 5 such that they appear at any desired distance. For example, an eye chart displayed on the display 22 can be generated to appear at a distance of 20 feet (standard ophthalmic eye testing distance for such test). The operation of the display 22 is known to those in the virtual reality applications. Much of the development in such technology has been driven by the gaming world, such as Oculus VR, Inc. who is dedicated to the development of immersive "virtual reality technology that's wearable and affordable." In most testing protocols the virtual reality simulations are quite rudimentary by the gamer standards as the stimulus is often a single dot or simple letter or symbol. However virtual reality currently available allows the goggles of the system 10 of FIGS. 3 and 4A-B to immerse the subject 5 into any desired scenario such that the testing protocols for the system 10 of FIGS. 3 and 4A-B are not limited.

Figure 4A:
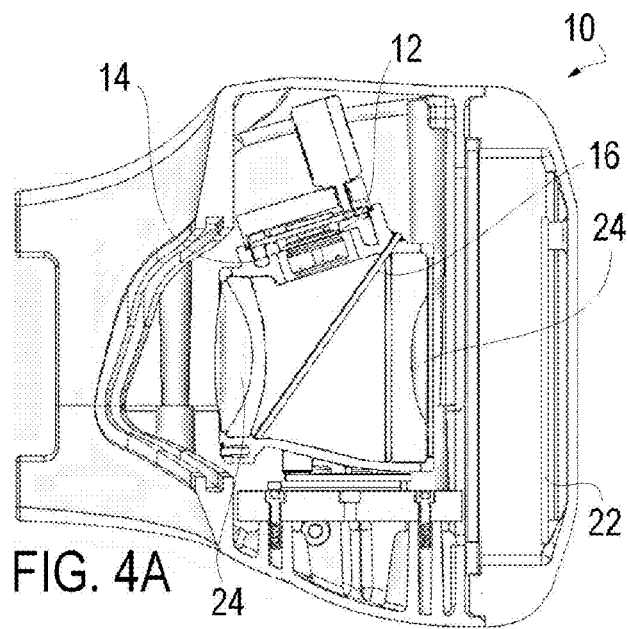
FIGS. 4A and B are schematic views of a head mounted closed goggle based video oculography system (VOG) system with integral stimulus screen in accordance with one aspect of the present invention.

FIGS. 4A and B are schematic views of a head mounted closed goggle based video oculography system 10 with integral stimulus screen 22 in accordance with another aspect of the present invention. The system 10 of FIGS. 4A and B uses a compact integrated optics 24 and hot mirror unit 16 with top mounted cameras 12. The system 10 of FIGS. 4A and B uses a single-screen 22 design shown in the FIGS. 4A and B that provides a head mounted goggle based VOG system 10 with onboard display 22 and compact integrated optics 24 and hot mirror unit 16. One key aspect of the design of system 10 of FIGS. 4A and B is using a first "camera" optic or lens 24 in front of the angled hot mirror 12 and a separate display optic or lens 24 behind the angled hot mirror 12 that is associated solely with the display 12. The display optics that transmits the image of display 22 to the subject's eye 7 is technically the combination of the camera optic 24 and the display optics 24. The separate front and rear optics 24 as shown allows the system 10 to accommodate the necessary camera field for cameras 12 and the display field for display 22 without undue distortion while remaining a compact system as shown. The compact system allows for simple gross adjustment of the optic position relative to the user via a rack and pinion adjustment or similar adjustment.

Figure 5:
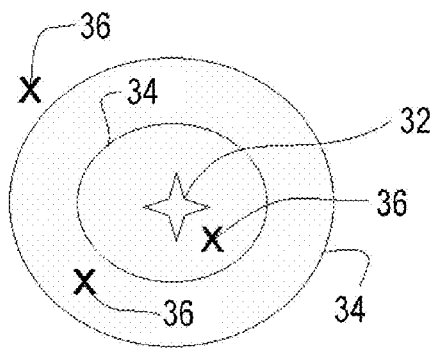
FIG. 5 schematically illustrates a visual fixation target for eye evaluation applications requiring subject compliance with eye fixation to the visual fixation target and schematically illustrates validation thresholds and sample subject's calculated gaze positions.

Objective Ophthalmic Eye Testing in Applications Requiring Subject Compliance with Eye Fixation One aspect of the present invention provides a method for validating testing procedure in objective ophthalmic eye testing for eye evaluation applications requiring subject compliance with eye fixation to a visual target 32 represented in FIG. 5. A representative test is peripheral vision testing in which the subject 5 is instructed to maintain gaze on the visual target 32 and the subject 5 is then displayed visual indicia in his peripheral vision, which presumes the subject 5 is maintain gaze upon the fixation target 32 throughout the testing.

The predetermined visual fixation target 32 is supplied to the subject 5 in a predetermined location with an automated ophthalmic eye testing device. The validation or compliance monitoring of the present invention is utilized in testing procedure of the eye evaluation application which requires the subject 5 to fixate upon the visual fixation target 5, such as peripheral vision testing. The display of the visual fixation target 32 and the peripheral stimulus may be on display 22 in the closed goggle system 10 of FIGS. 4A and B. Alternatively in the open system 10 of FIG. 3 the visual fixation target 32 may be generated by a separate display such as a laptop computer display screen (directly or projected onto a surface in front of the subject 5), or formed by image generating system such as the PURSUIT TRACKER® brand laser generating tool.

The system and associated method of the present invention includes tracking the subject's gaze during at least the supplying of the predetermined visual fixation target 32 to the subject 5 throughout the testing procedure of the eye evaluation application with a video based eye tracking system 10. Select gaze points 36 of the subject 5 are shown relative to the fixation target 32 for illustration. The gaze points 36 will not be randomly distributed but will generally form a scanpath as known in the art and the three points 36 shown represent distinct points 36 at spaced times along a scanpath for illustrative purposes. Additionally the present invention can compare each calculated gaze point 36 with the associated threshold 34 within the period of time the system 10 is obtaining each relative data point, or alternatively a collection of gaze points 36 within a segment of time associated with each relative data point maybe combined to form a single gaze point 36 for that segment. The combining of gaze points 36 within a segment of time could be by averaging all the gaze points 36 within a segment, or a weighted average, or by taking the maximum variation from the target 52 as the gaze point 36 for that segment.

The system and associated method of the present invention includes validating the testing procedure by at least one of i) indicating to the clinician when the subject's gaze location 36 differs from the predetermined visual fixation target 32 by an amount greater than a predetermined threshold amount 34, and ii) having the automated ophthalmic eye testing device repeat at least portions of the testing procedures when the subject's gaze location 36 differs from the predetermined visual fixation target 32 by an amount greater than a predetermined threshold amount 34. The system may do both the indication to the clinician and the automatic rerunning of data.

The real time display to the clinician of the results and the record of the session will include a visual indication that selected data sets are not validated due to failure of the subject's gaze 36 being within the desired threshold. Many visual indicating methods may be implemented, such as toggling between informative text associated with the data, for example VALID and INVALID, COMPLIANT and NON-COMPLIANT, nothing and FIXATION LOST and/or listing the associated difference between the gaze point 36 and the fixation target 34. Color coding may be added wherein red is used to visually identify non-compliance data and green illustrate validated data sets. Different indicators may be used on different displayed elements, for example a red border surrounding the recorded image of the subjects eye may be used on that screen with text in the boarder, and in graphical representation of data, non-validated data sets may simply be omitted from the graph or highlighted in red or otherwise identified.

The step of having the automated ophthalmic eye testing device repeat at least portions of the testing procedures when the subject's gaze location 36 differs from the predetermined visual fixation target 32 by an amount greater than a predetermined threshold amount 34 may be at the discretion of the clinician, who in real time during the test (or in setting up the system operation for the test) can indicate that it is desired to obtain validated data and the testing should continue. The repeating of the testing procedure may be of individual segments or it may require restarting from the beginning depending upon the particular protocol. The system may allow the clinician to selectively override the re-running of the testing protocol, such as where the clinician believes that sufficient data has been collected despite the non-compliance or where the clinician believes further data collection may be counter-productive due to stress on the subject or a variety of possible reasons.

As shown in FIG. 5 the predetermined threshold amount will depend upon the particular eye evaluation procedure and the associated desire for accuracy for valid results. For example peripheral vision testing may have a threshold 34 of greater than about one degree, while retinal eye segment mapping procedures will have a threshold 34 much less than one degree.

Two relative thresholds 34 are shown in FIG. 5. As illustrated the calculated gaze positions 36 shown will have two data points within the broader threshold 34 and the present system will validate the testing results for those two data points using the broader threshold 34 while indicating to the clinician that the third is not a valid result and/or rerunning the testing protocol for the third data point until acceptable results are obtained (i.e. until the gaze point 36 calculated for the associated data is within the broader threshold 34). The test associated with the narrower threshold will analogously only validate the one data point and indicate to the clinician that the subject's gaze location 36 differs from the predetermined visual fixation target 32 by an amount greater than the predetermined threshold amount 34 for the two outlaying data points, and/or the system will have the automated ophthalmic eye testing device repeat at least portions of the testing procedure for the two non-complying data point where the subject's gaze location 36 differs from the predetermined visual fixation target 32 by an amount greater than the predetermined threshold amount 34. Additionally, not only may the threshold 34 differ from test to test, the threshold need not be the same in all directions (i.e. not represented as a circle around the fixation target 32). For example compliance may be more restrictive along one axis than the other resulting in an elliptical type shape for the predetermined threshold amount 34.

The system and method for validating testing procedures in objective ophthalmic eye testing requiring subject 5 compliance with a fixation target may have the predetermined visual fixation target 32 supplied at a static location throughout the testing procedure. However it is anticipated that the predetermined visual fixation target 32 supplied at predetermined varied locations throughout the testing procedure. The moving of the fixation target 32 throughout a testing procedure can yield more complex eye evaluation procedures. Additionally some conventional tests, such as a swinging flashlight test, use what can be termed as a moving fixation target. A moving fixation target 32 may be used with a stimulus that is necessary to maintain tight control over the shape and/or lumen and/or color of the stimulus. Using a moving fixation target 32 can allow the stimulus to be maintained in the same location and thus help maintain stimulus consistency which could be particularly beneficial in retinal/eye mapping protocols wherein the mapping is of the response to distinct portions of the eye being subjected to the same stimulus.

It is important to emphasize that the present method and associated apparatus deals with eye evaluations requiring subject compliance with eye fixation to a visual target 32. These tests are distinctly different from testing protocols that are actually measuring eye response in the form including gaze distance from a stimulus target, such as a smooth pursuit test, in which the subject's inability to maintain visual gaze on the stimulus target does not invalidate the test (but actually is part of the desired data results of the testing protocol). The present method and apparatus are directed to that family of tests in which the meaningful test data assumes and requires the subject compliance with maintaining gaze on the target 32. Further there are tests in which the target 32 is only relevant for a portion of the testing protocol, and the present method and apparatus operate as described for that portion. For example one spontaneous nystagmus test requires the subject to focus on a target 32 which will disappear and the testing is viewing the drift of the eye from the position where the target 32 was presented. In this testing procedure the validation step of the invention is at the beginning of the test while the target 32 is visible.

The apparatus and method for validating testing procedure in objective ophthalmic eye testing according to invention, may in some testing protocols, have the predetermined visual fixation target 32 form the stimulus for at least a portion of the testing procedure, such as a swinging flashlight test. The system 10 may further record pupillary responses of the subject's eyes 7 during at least the supplying of the predetermined visual fixation target 32 to the subject 5. The video based eye tracking system 10 can further record physiologic data, such as head position or any desired data, in addition to gaze 36 of the subject's eyes 7 during at least the supplying of the predetermined visual fixation target 32 to the subject 5.

Stable Pupillometry Parameters

Figure 6:
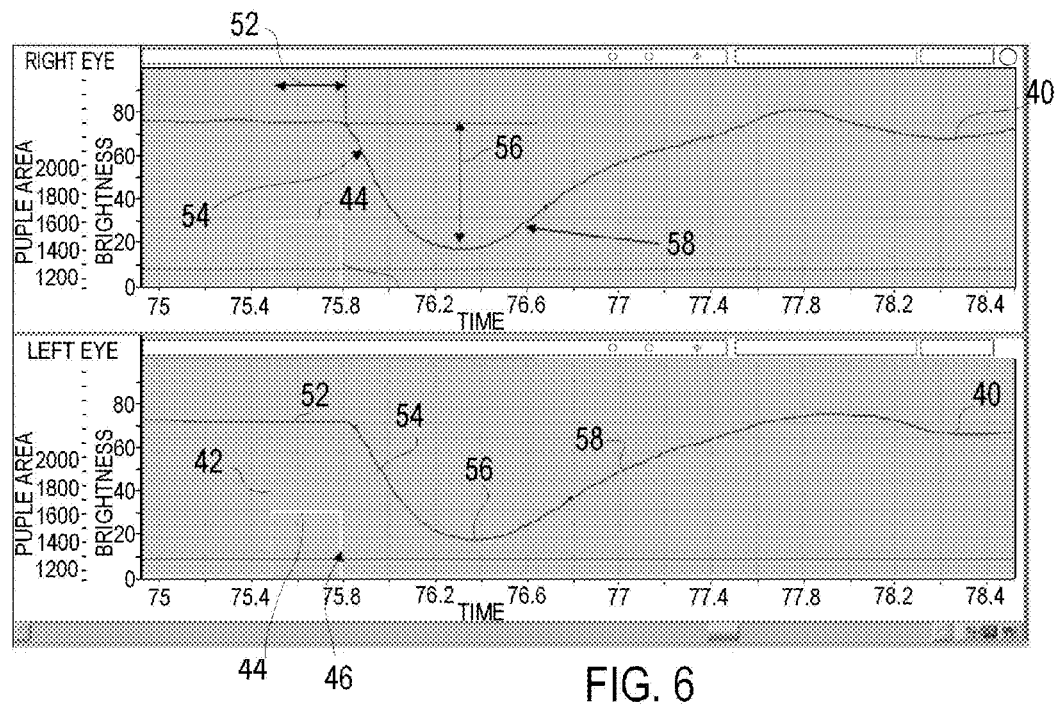
FIGS. 6 and 7 are eye position graphs illustrating pupilometry parameters obtained for measuring and analyzing ocular response with the system according to one embodiment of the present invention.
Figure 7:
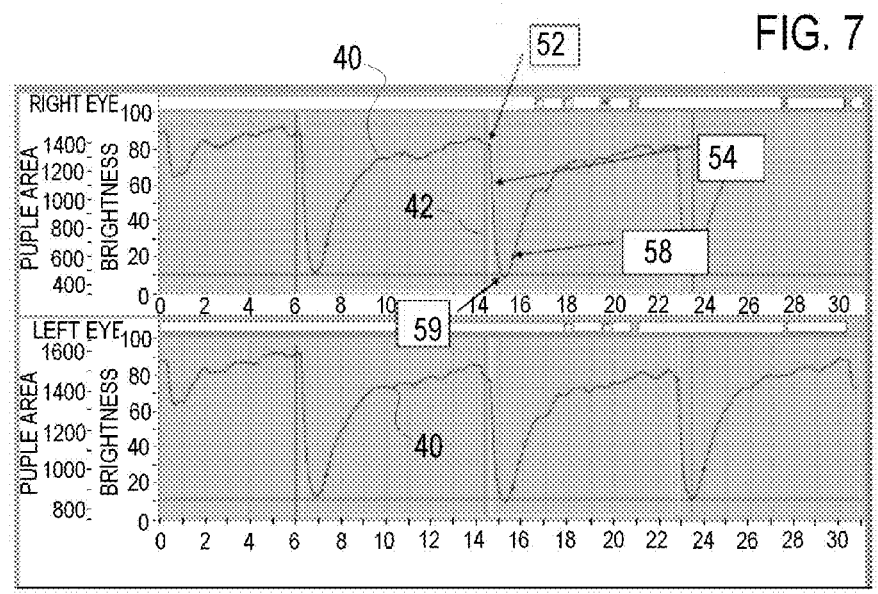

Pupil measurements as objective ophthalmic eye testing results are well known and a number of standard tests are utilized to evaluate pupilary response. A VOG system 10 provides objective results to such testing. FIGS. 6 and 7 are eye position graphs 40 relative to time illustrating pupilometry parameters (52, 54, 56 and 58) obtained for measuring and analyzing ocular response with the system 10 according to one embodiment of the present invention. Conventional pupilometry measurements in the art include generally the amplitude 56 of the change to pupil size (diameter), i.e. what is the size of the pupil after stimulation or after the stimulation is removed, or even more basically whether such a change is occurring at all, and occasionally the latency 52 of the response is included.

The present invention provides that constriction 54 and re-dilation 58 velocity of pupil are more stable biomarkers than previously utilized parameters. The re-dilation 58 may also simply be referenced as a dilation velocity 58 of the pupil. Pupil constriction 54 and re-dilation 58 velocities are radial pupil rate of change measurements. High speed Video Oculography, wherein high speed means at least 60 hz, typically at least 100 hz (and 250 hz and 500 hz systems are currently available) allows for measuring constriction 54 and re-dilation 58 velocity of pupil. Pupil constriction and re-dilation acceleration, which is the derivative of constriction 54 and re-dilation 58 velocity curves is also a relevant bioindicators and believed to represent further stable bio-indicator for Pupilometry measurements, although accurate Pupilometry acceleration measurements may require higher operating sample camera/system speeds of 250 Hz or more.

Pupil constriction 54 and re-dilation 56 velocity much more stable than amplitude 56 of dilation or pupil response latency 52, which is time between the beginning 42 of the stimulus 44 and eye movement. As shown in FIGS. 6 and 7 it can be helpful if the stimulus 44 is graphed along with eye position so that the beginning 42 time and the ending 46 time of the stimulus is readily observed on the chart, however is such dual graphing the horizontal axis for the stimulus will typically not be eye position but another parameter, such as lumens or brightness of the stimulus. Additionally the pupil constriction 54 and re-dilation 58 velocity and acceleration parameters can be considered more sensitive biomarkers for evaluation purposes. These velocities 54, 58 and acceleration calculations will improve with higher speeds up to around 500 hz, with diminishing returns on improved velocity or acceleration calculations after that as these speeds far exceeds the measured response. As noted the system 10 typically records each eye 7 response of a subject 5 individually.

Figure 8:
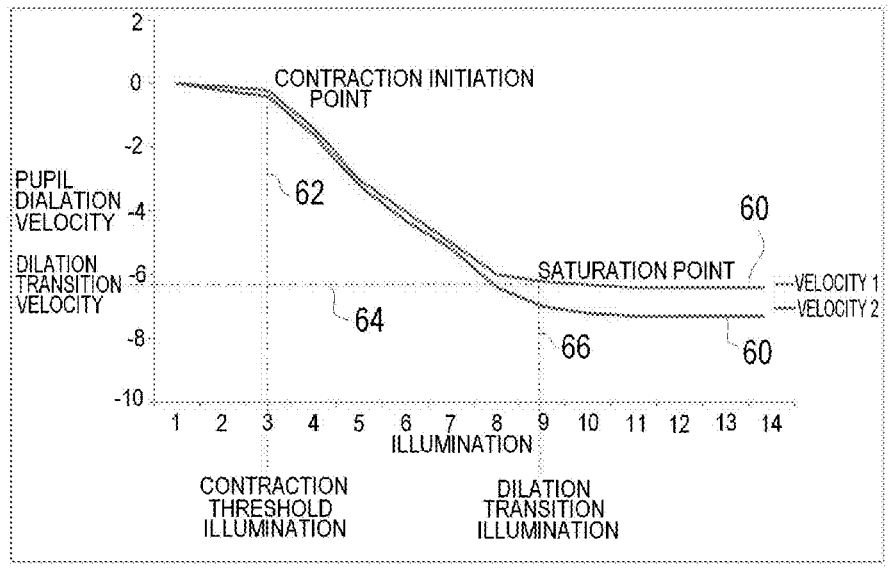
FIG. 8 is an eye saturation graph illustrating pupilometry parameters associated with pupil dilation velocities and stimulation illumination which are obtained for measuring and analyzing ocular response with the system according to one embodiment of the present invention.

FIG. 8 is an eye saturation graph 60 illustrating pupilometry parameters (62, 64, 66) associated with pupil dilation velocities and stimulation illumination which are obtained for measuring and analyzing ocular response with the system 10 according to one embodiment of the present invention. Essentially the eye saturation data found in graph 60 for a given eye 7 of a subject is found by providing a number of stimuli, individually, to the subject at increasing illumination amounts (increasing lumens or brightness). As shown in FIG. 8, for very low illuminations (i.e., dim stimulus) the subject's eye 7 will not exhibit significant constriction velocity 54, until the stimulus reaches a contraction threshold illumination 62, above which each stimuli will generate a position graph similar to that shown in FIGS. 6-7 (without re-dilation). The precise contraction threshold illumination 62 may be selected as the inflection point in the graph 60 or after when a given constriction velocity is obtained, or a given rate of change of the velocity, all of which will be generally known to those of ordinary skill in the art in parsing similar physiologic parameter data. From the point of the contraction threshold illumination 62 the eye response to increasing lumens or brightness of the stimuli will yield a faster pupil constriction velocity (shown as negative values in FIG. 8 as it is for constriction) until about the saturation point which corresponds to a stimulus illumination at the dilation transition illumination 66 and a maximum (absolute) constriction velocity identified as the dilation transition velocity 64. The precise location of the saturation point may be at the lower inflection point of the curve, or where the curve reaches a predetermined shallowness, which precise calculation will generally be known to those of ordinary skill in the art. The graphs 60 will typically be done for each of the subject's eyes 7.

The saturation based pupilometry parameters 62, 64, and 66 may be particularly helpful is addressing certain characteristics, such as objectively identifying light sensitivity of a subject 5. Further large disparities between left and right eyes 7 of a subject of the curve 60 and associated parameters 62, 64 and 66 is indicative of issues to be addressed with the subject 5, for example it can be used as a reliable indicator of mTBI for those who have experienced head trauma. A larger contraction illumination threshold 62 will objectively identify vision issues, possibly before other testing does so. The relative values of the dilation transition velocity 64 and the dilation transition illumination 66 can also be valuable biomarkers as these objectively measure the effective pupil velocity limits at which the subject's eye 7 can react, and the illumination at which such is reached.

The method of measuring and analyzing an ocular response in a subject 5 using stable pupilary parameters includes providing a video oculography based system 10 for the subject 5 with the video oculography system configured to collect eye images of the subject 5 in excess of at least 60 hz and configured to resolve eye movements smaller than at least 3 degrees of motion. As discussed above, higher camera 12 speeds and greater accuracy in measurement is preferred, subject to cost considerations. Providing a system 10 configured to resolve eye movements smaller than at least 2 degrees of motion or even smaller than 1 degrees of motion is also preferable subject to costs and processing speeds. The system 10 shown in FIGS. 3-4A-B provides a system operating above 200 Hz (240 Hz) and configured to resolve eye movements smaller than at least 0.1 degrees of motion.

The apparatus and method of the invention provides for collecting eye data with the video oculography based system 10 wherein at least one stimulus is presented to the subject 5 and configured to yield a pupil eye response from at least one eye 7 of the subject 5. The apparatus and method of the invention calculates pupilometry measurements (40, 52, 54, 56, 58, 60, 62, 64 and 66).

The pupilometry measurements include average pupil constriction velocity 54 for subject's eyes 7, wherein the average pupil constriction velocity 54 for subject's eyes is the average of the subject's eyes total amplitude of pupil constriction 56 following a stimulus display divided by the length of time (from 52 to 56) the associated pupil is undergoing constriction following the start 42 of the stimulus display. The pupilometry measurements include maximum pupil constriction velocity (also marked as 54) for subject's eyes, wherein the maximum pupil constriction velocity 54 for subject's eyes is the maximum calculated pupil constriction velocity 54 of the subject's eyes 7 following a stimulus display. The maximum pupil constriction velocity 54 can be considered to be the maximum slope of the curve 54. Other methods of calculating and implementing pupil constriction velocity 54 are possible such as dividing the curve 54 into discrete segments and using the average constriction velocity for each segment.

The pupilometry measurements include average pupil dilation velocity 58 for subject's eyes 7, wherein the average pupil dilation velocity 58 for subject's eyes 7 is the average of the subject's eyes 7 total amplitude of pupil dilation following the end 46 of a stimulus display 44 divided by the length of time the associated pupil is undergoing dilation following the termination of a stimulus display. The pupilometry measurements include maximum pupil dilation velocity 58 for subject's eyes 7, wherein the maximum pupil dilation velocity 58 for subject's eyes 7 is the maximum calculated pupil dilation velocity 58 of the subject's eyes following the termination of a stimulus display. The maximum pupil dilation velocity 58 can be considered to be the maximum slope of the curve 58. Other methods of calculating and implementing pupil dilation velocity 58, like constriction velocity 54, are possible such as dividing the curve 58 into discrete segments and using the average constriction velocity for each segment.

The pupilometry measurements include the pupil constriction acceleration for subject's eyes 7, wherein the pupil constriction acceleration for subject's eyes is the rate of change of the calculated pupil constriction velocities 38 following the stimulus display 44. The pupilometry measurements include pupil dilation acceleration for subject's eyes 7, wherein the pupil dilation acceleration for subject's eyes 7 is the rate of change of the calculated pupil dilation velocities 38 following the termination of a stimulus display. The acceleration parameters obviously cannot be based upon the average velocity parameters discussed above or an acceleration of zero will result, and not be particularly meaningful.

The pupilometry measurements include at least one pupil saturation parameter (60. 62, 64 and 66), wherein each pupil saturation parameter for subject's eyes 7 is a physiologic measurement associated with pupil dilation velocity 58 when the eye is subjected to a stimulus 44 of a given illumination. Preferably the maximum constriction velocity 54 discussed above is used for developing the curve 60 and the associated pupil saturation parameters 62, 64 and 66, however average constriction velocity could also be utilized.

The method and associated apparatus of the present invention provides for analyzing a subject's ocular response based upon at least one of the calculated pupilometry measurements disclosed herein.

The method and associated apparatus of measuring and analyzing an ocular response in a subject according to the invention may provide that the pupil measurements are calculated independently for the subject's left and right eyes 7 for each stimulus presented to the subject. The method of measuring and analyzing an ocular response in a subject 5 according to the invention may further including the step of calculating comparative left and right pupilometry measurements from the eye data including at least one of: i) comparative pupil constriction velocity for subject's eyes, wherein the comparative pupil constriction velocity for subject's eyes is the difference or ratio between the subject's calculated left eye average pupil constriction velocity and the subject's right eye average pupil constriction velocity following the stimulus display; ii) comparative pupil dilation velocity for subject's eyes, wherein the comparative pupil dilation velocity for subject's eyes is the difference or ratio between the subject's calculated left eye average pupil dilation velocity and the subject's right eye average pupil dilation velocity following the termination of the stimulus display; iii) comparative maximum pupil constriction velocity for subject's eyes, wherein the comparative maximum pupil constriction velocity for subject's eyes is the difference or ratio between the subject's calculated maximum pupil constriction velocity of the subject's left eye and subject's calculated maximum pupil constriction velocity of the subject's right eye following a stimulus display; iv) comparative maximum pupil dilation velocity for subject's eyes, wherein the comparative maximum pupil dilation velocity for subject's eyes the difference or ratio between the subject's calculated maximum pupil dilation velocity of the subject's left eye and subject's calculated maximum pupil dilation velocity of the subject's right eye following the termination of the stimulus display; v) comparative pupil constriction acceleration for subject's eyes, wherein the comparative pupil constriction acceleration for subject's eyes is the difference or ratio between the subject's calculated pupil constriction acceleration of the subject's left eye and subject's calculated pupil constriction acceleration of the subject's right eye following the stimulus display; vi) comparative pupil dilation acceleration for subject's eyes, wherein the comparative pupil dilation acceleration for subject's eyes is the difference or ratio between the subject's calculated pupil dilation acceleration of the subject's left eye and subject's calculated pupil dilation acceleration of the subject's right eye following termination of the stimulus display; and vii) at least one comparative pupil saturation parameter for subject's eyes, wherein the comparative pupil saturation parameter for subject's eyes is the difference or ratio between the subject's calculated pupil saturation parameter of the subject's left eye and subject's calculated pupil saturation parameter of the subject's right eye. Further, the step of analyzing a subject's ocular response is based upon at least one of the calculated comparative pupilometry measurements.

As discussed further below, the method and associated apparatus of measuring and analyzing an ocular response in a subject according to invention may provide that each stimulus 44 is presented to only one eye 7 of the subject 5 while the parameters are obtained from both.

The method of measuring and analyzing an ocular response in a subject according to invention may further including the step of calculating comparative constriction-dilation pupilometry measurements from the eye data including at least one of: i) comparative pupil constriction-dilation velocity for subject's eyes, wherein the comparative pupil constriction-dilation velocity for subject's eyes is the difference or ratio between the subject's calculated average pupil constriction velocity and the subject's calculated average pupil dilation velocity following the stimulus display; ii) comparative maximum pupil constriction-dilation velocity for subject's eyes, wherein the comparative maximum pupil constriction-dilation velocity for subject's eyes is the difference or ratio between the subject's calculated maximum pupil constriction velocity of the subject's eyes and subject's calculated maximum pupil dilation velocity of the subject's eyes following a stimulus display; and iii) comparative pupil constriction-dilation acceleration for subject's eyes, wherein the comparative pupil constriction-dilation acceleration for subject's eyes is the difference or ratio between the subject's calculated pupil constriction acceleration of the subject's eyes and subject's calculated pupil dilation acceleration of the subject's eyes following a stimulus display. The method of measuring and analyzing an ocular response in a subject according to invention may provide that the step of analyzing a subject's ocular response is based upon at least one of the calculated comparative pupilometry measurements.

Video Oculography Monitoring Both Eye Pupillometry with Stimulus in Only One Eye High speed Video Oculography allows for measuring response in both eyes 7 while stimulating only a single eye 7 of the subject 5. Essentially the non stimulated eye 7 is occluded, but VOG systems 10 can obtain eye responses from such non stimulated eye 7 during the testing protocols. The present invention provides monitoring eye response relative to each other as only a single eye is being stimulated and a comparison of the responses, such as a ratio of values and/or a difference of values. The non-stimulated eye response parameters and comparisons of such to the stimulated eye parameters represent a significant biomarker and indicator of area of damage of neural network.

The stimulus to the one eye 7 may be visual (44) as generally known, or may also be a pressure stimulus or a temperature stimulus or combinations thereof. The pupilary parameters to be compared between the stimulated eye response and the response of the non stimulated eye include amplitude of pupilary response, latency of the pupilary response, velocity of pupilary constriction and re-dilation and acceleration of pupilary constriction and re-dilation. The comparison parameter may be either (1) the difference between the two, i.e. the value of the stimulated eye minus the value of the non stimulated eye for each parameter, or (2) the ratio between the two, i.e. the value of the stimulated eye divided by the value of the non stimulated eye for each parameter (or the inverse).

High Speed VOG System 10 Synchronization

Many of the above described physiologic test parameters, that could serve as effective stable biomarkers, represent physiologic parameters only obtainable with a high speed devices, and thus only became possible in VOG systems 10 with cost effective high speed cameras. These parameters, and other "high speed parameters" such as second order or higher corrective saccadic eye movements, micro-saccades, etc, raise a new issue with such systems, namely the synchronization of the actual timing of the visual stimulus with measurements associated with that timing.

Basically these high speed parameters can become inaccurate due to the processing delays within the conventional computer without a synchronization system. The present invention allows accurate cost effective synchronization of the acquired eye images with the presentation of stimuli on a screen 22. This synchronized timing is critical for measuring accurate high speed latencies, velocities and certainly accelerations.

Figure 9A:
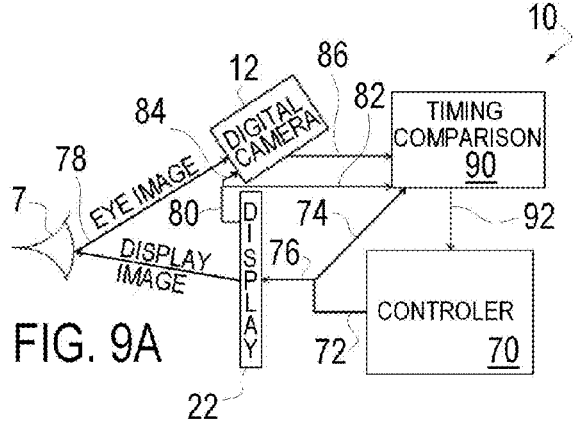
FIG. 9A-C schematically illustrate system synchronization configurations for use with the system according to one embodiment of the present invention.
Figure 9B:
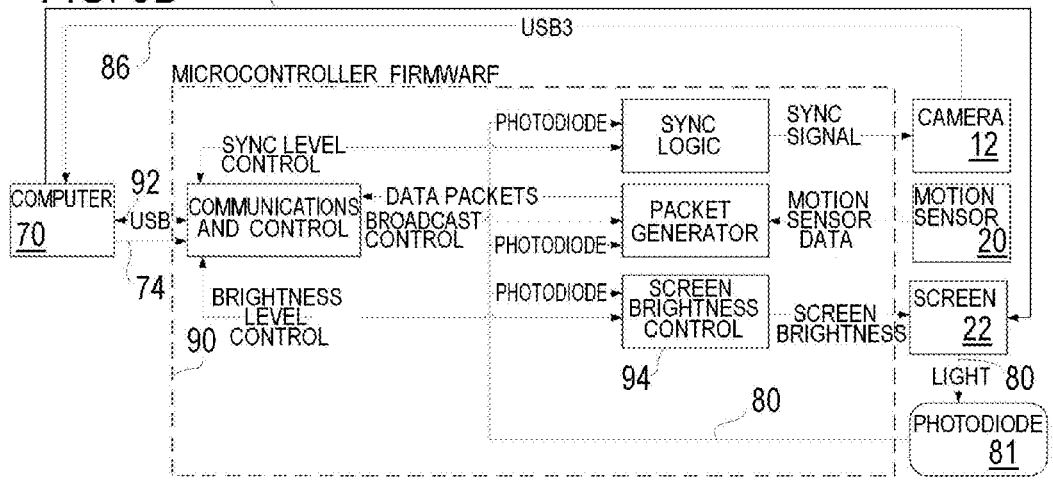
Figure 9C:
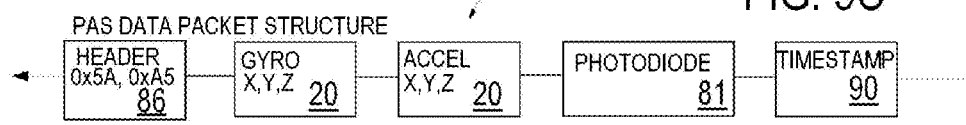
Figure 12A:
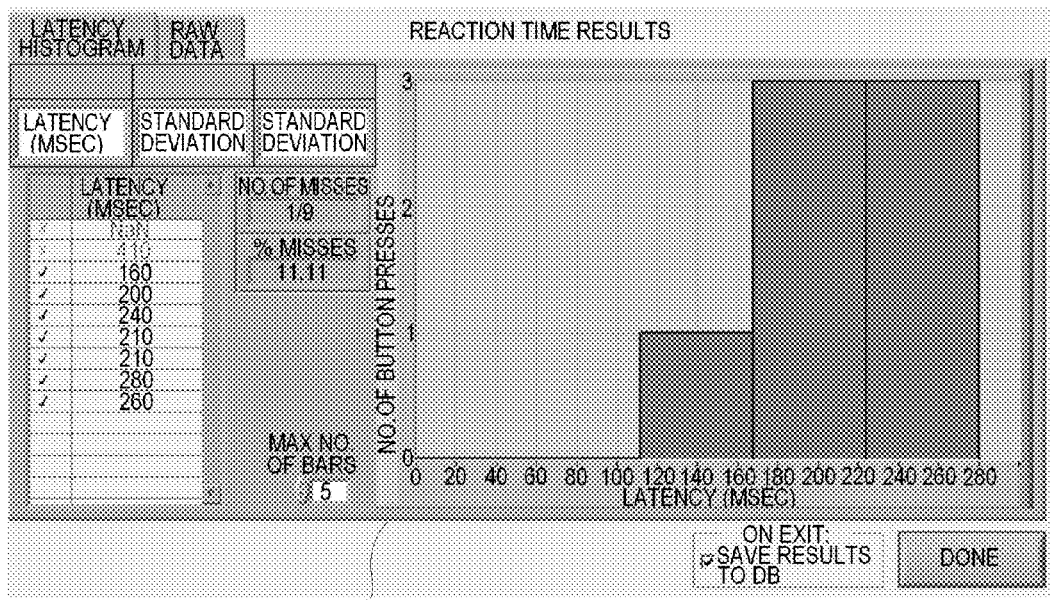
Figure 12B:
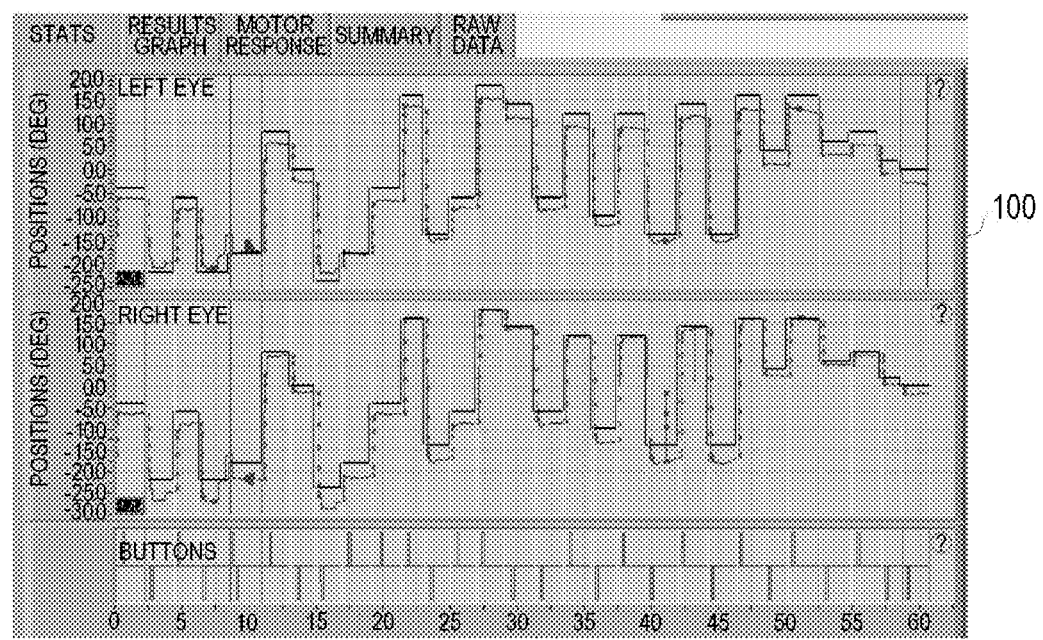
Figure 12D:
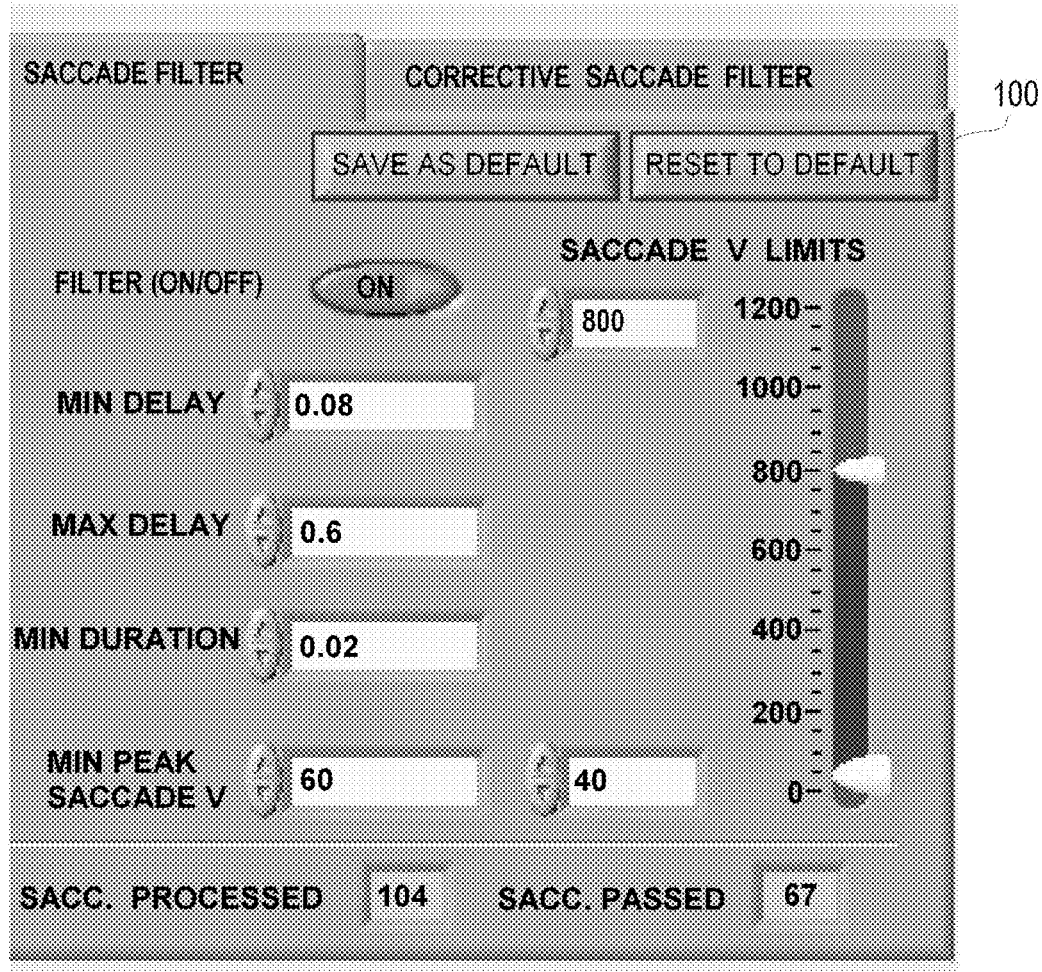
Figure 12E:
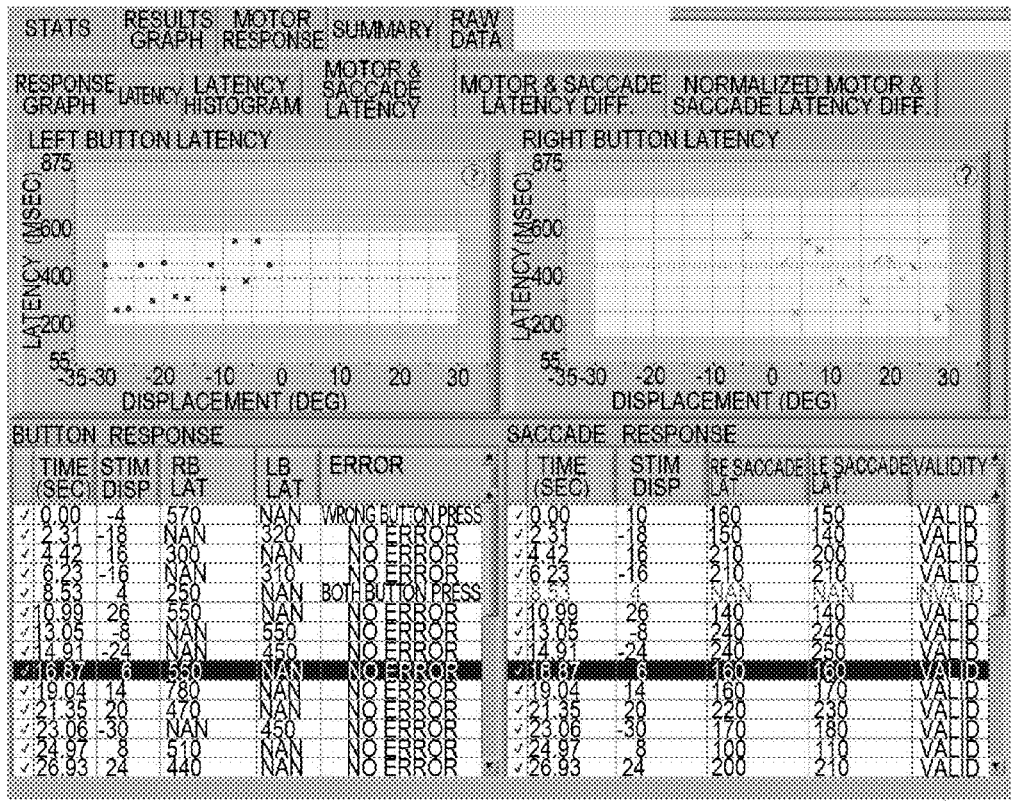
Figure 12F:
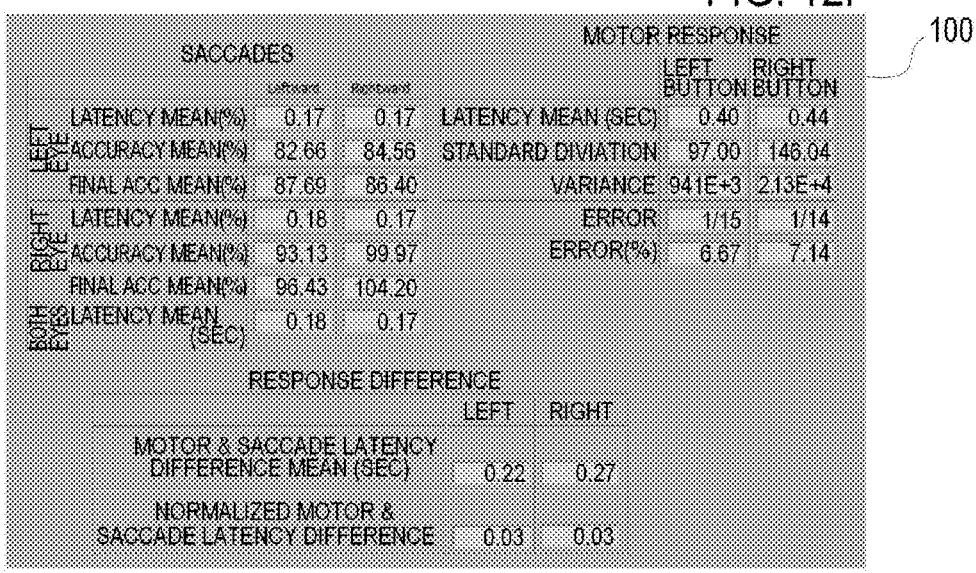
Figure 14A:
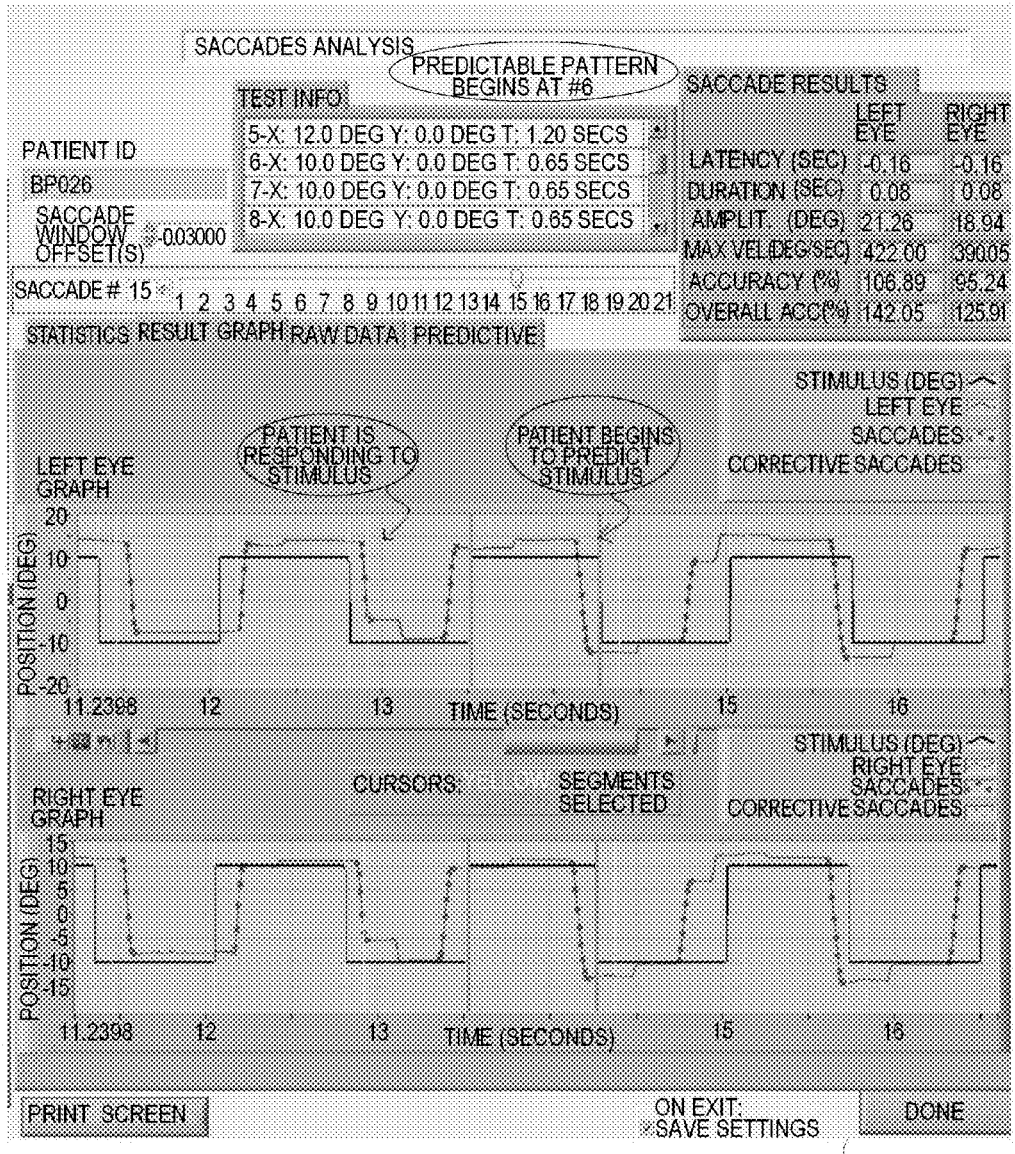
FIGS. 14A-D illustrate display results and control parameters associated with Predictive saccade response testing protocol according to one embodiment of the present invention.
Figure 14B:
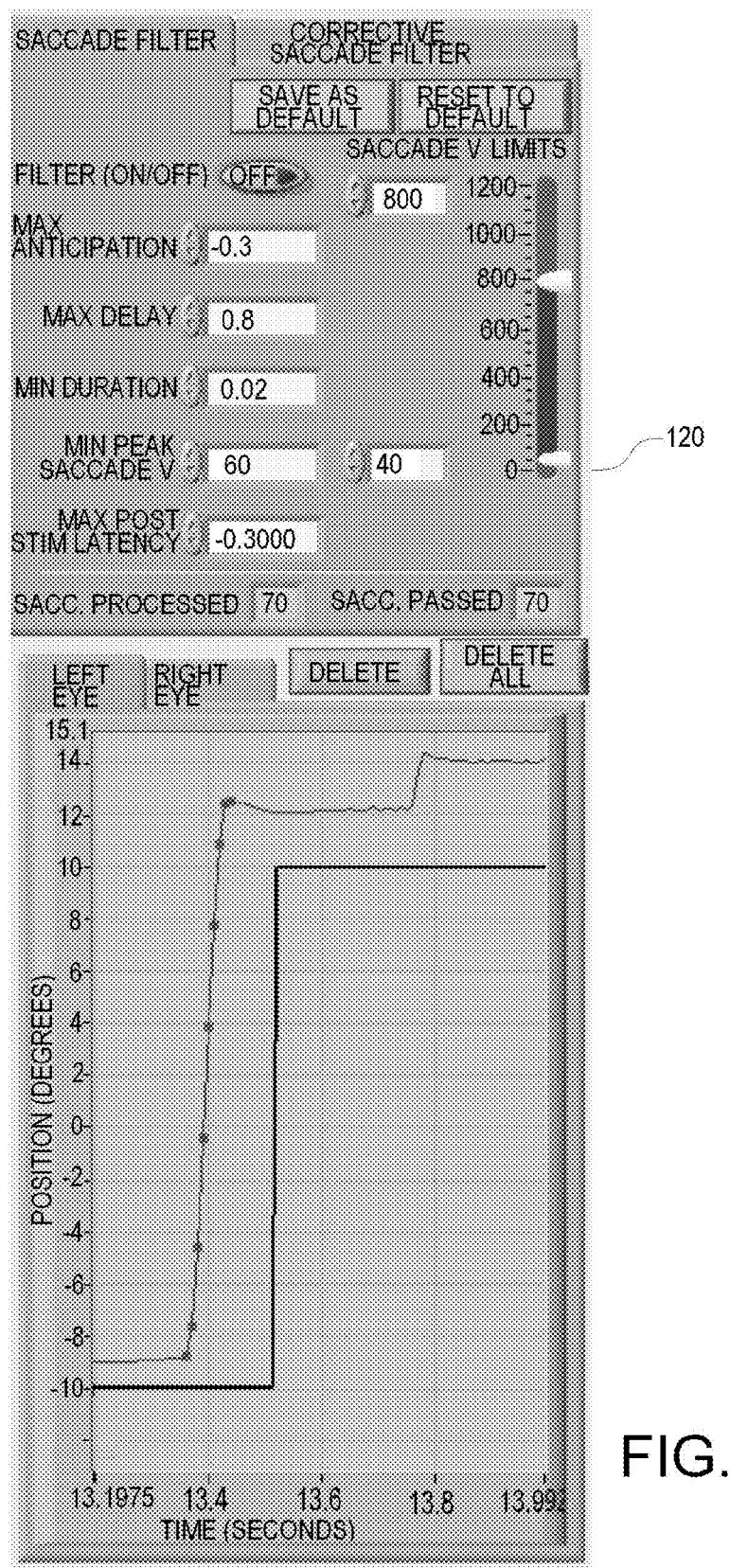
Figures 14C, 14D:
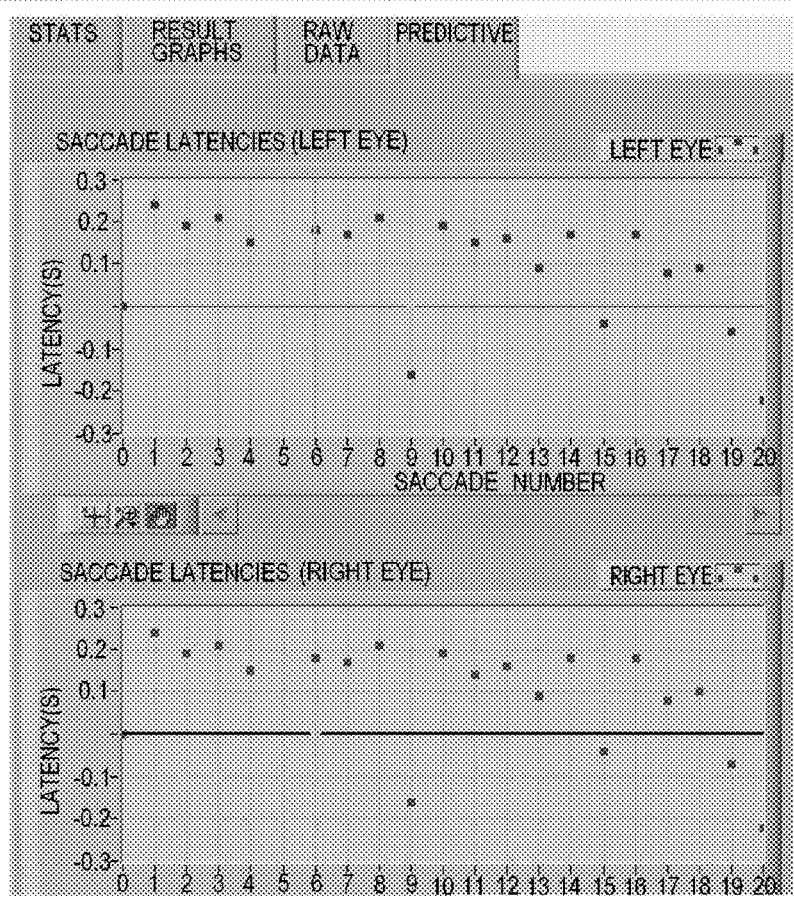

The present invention proposes several simple synchronization protocols that are particularly cost effective. FIG. 9A-C schematically illustrates system synchronization configurations for use with the system according to the present invention. Turning to FIGS. 9A and 9B, the OLED microdisplays 22 used in the onboard display application are driven by a VGA signal 72 from the controller 70 (in an associated PC). The VGA signal 72 contains red, green, and blue image components and FIG. 10A schematically illustrates a video representation of the video synchronization signal 72 for use with the system according to one embodiment of the present invention. The present synchronization system diverts one of the lines, i.e. the "blue line", to the timing comparison unit 90, also called a custom synchronization board (comprised of the synchronization logic module and the packet generation module as shown in FIG. 9B). Whenever the system 10 indicates a stimulus is to be output from the controller 70 (PC) to present on-screen 22 to the subject 5, such as a red dot for a saccades test, the synchronization method of the invention can render video synchronization signal 72 with a large blue bar (or any visible element) in the background as the synchronization indicia. As shown in FIGS. 9A and B, the synchronization portion 74 (the blue portion of the signal) of the video synchronization signal 72 is diverted to the timing comparison unit 90. The timing comparison unit 90, also referenced as the synchronization board, sees the voltage in the blue-signal line increase via signal 74 and is configured to output a logic signal indicating this signal.

This logical signal from the timing comparison unit 90 (the blue-sync board) is paired with the eye images and other data and returned to the controller 70 (PC) for analysis as shown in FIG. 9C. The controller 70 renders video based synchronization signals (72, 74), e.g. the blue bars, at key moments during testing so the system can accurately determine, exactly when the visual stimulus (the dot) reaches the end of its travel in a smooth pursuit test or appears on-screen 22 in a reaction-time test. The subject does not see the blue bar synchronization indicia because the blue color line 74 has been diverted to only the custom synchronization board. Variations of this invention could use other color lines or could maintain the ability to display the color on-screen to the subject.

This synchronization method, called the blue sync method herein, is independent of other synchronization schemes implemented and can be utilized alone to synchronize VOG systems. However the present invention discloses two other synchronization methodologies that each may be used in conjunction with the blue sync method or used independently. Each of these methodologies are shown in FIG. 9A.

This system provides independent synchronization through the use of a photodiode 81 attached to the display screen 22. The controller rendering the stimulus display in signal 76 will create visible synchronization pulses that the photodiode 81 will pick up generally as signal 80 in FIG. 9A. The synchronization pulses in signal 76 and the photodiode are preferably directed to portions of the display 22 outside the field of view of the subject 5. Photodiode output is directed via line 82 to the timing comparison unit 90 and is combined with the images from cameras 12 and also combined with the data from the motion sensor 20 as part of the data packet that this system outputs to the computer controller 70. This means is that data collected from the motion sensor 20 and data collected from the eye via cameras 20 can then be aligned to the stimulus data so that accurate calculations can be performed by the controller.

The photodiode 81 provides an advantage of additional functionality, namely the ability to calibrate the screen brightness using the photodiode 81 coupled to a brightness controller 94 (which is separate functionally from the timing comparison unit 90 but may be considered a part thereof) to ensure that the screen 22 is also set to a correct brightness. This can help correct for aging screens 22 and is important for light reflex tests and pupil saturation tests which rely on the light output of the screen 22. The rate at which the data packets are sent to controller 70 is controllable from a range of every 255 ms to 1 ms. This means the output rates of up to 1000 Hz is possible. This allows for as accurate photodiode 81 sampling as possible.

The photodiode-timing comparison unit synchronization can operate independently of the blue sync method discussed above, or in conjunction therewith. If used in conjunction with each other the sync logic will prioritize the distinct timing signals 74 and 82.

This system provides third synchronization through the use of a photodiode 81 attached to the display screen 22, in which the signal 80 from the photodiode is paired via signal 84 to the eye data in camera 12 via a general purpose input pin on the digital camera 12 that is tracking the eye. In this synchronization scheme the images from the camera will have the synchronization signals 84 from the photodiode incorporated therein and the packet structure will include the embedded synch signals in the video image from the camera at line 86. The photodiode signal embedded in camera output synchronization method can operate independently of the blue sync method discussed above, or in conjunction therewith. Further, although a common photodiode 81 is used in both, the photodiode signal embedded in camera output synchronization method is considered independent from the photodiode-timing comparison unit 90 synchronization method as each can be individually used or used in conjunction. If used in conjunction with each other the controller will prioritize the distinct timing signals added in the packet data 92 and embedded within the camera image thereon.

Each of these synchronization methods have distinct advantages, and thus it may be beneficial if they are used in conjunction with each other. As an alternative to the photodiode 81, a fiber optic line may be used in its place. Like the photodiode 81 the fiber optic line 80 can run to the timing comparison unit 90 via line 82, with some optical sensor therein converting the optical signals to electrical signals for the synch logic and the packet generator. Additionally the fiber optic line 80 can run via line 84 to the camera to be embedded directly into the images obtained by the camera 12. The line 84 can merely go to the front of the lens in a desired location for obtaining video synchronization signals, or bypassing the lens and be directly embedded in a portion of the image by the camera controller. The use of fiber optic line synchronization will allow for greater synchronization data to be added in video signal 76, such as sequential numbering of the "frames" or other desired information.

In summary the synchronization apparatus of the present invention may be summarized as a video oculography based neuro-otologic testing and evaluation system comprising: A base adapted to be positioned adjacent to a subject's head; At least one digital camera 12 attached to the base, operating at least at 60 frames per second and configured to take images of at least one of the subject's eyes 7; A display 22 for selectively displaying visual stimulus to the subject 5; A controller 70 coupled to the display 22 generating each visual stimulus to be displayed and coupled to each digital camera 12 and receiving and storing data signals there from, the controller 70 configured to calculate eye related data from the digital camera images, and configured to display the eye related data to users; A video synchronization signal 72, 76, and 74 generated by the controller 70 associated with each visual stimulus which identifies when the display 22 is displaying the associated visual stimulus to the subject 5; Receiving and coupling the video synchronization signal with at least the eye data from the digital camera, wherein the received video synchronization signal and the eye data from the digital camera are utilized by the controller 70 to synchronize calculations based upon the eye data and the visual stimulus.

The video oculography based neuro-otologic testing and evaluation system according to the invention provides in one embodiment that the system further includes a photodiode 81 or fiber optic line coupled to the display screen 22, wherein the photodiode or fiber optic line receives the video synchronization signal 76 from the display 22. The synchronization system according to one embodiment may provide that the controller creates the video synchronization signals as synchronization pulses of video display elements of the display which are received by the photodiode or fiber optic line. The synchronization system according to one embodiment may provide wherein the photodiode signals 84 associated with the video synchronization signals is paired to the eye data via an input on the digital cameras 12.

The video oculography based neuro-otologic testing and evaluation system according to the invention may be provided such that the controller uses data from a photodiode 81 coupled to the display screen 22 to calibrate the brightness of the display 22.

As discussed above the synchronization system used in the video oculography based neuro-otologic testing and evaluation system according to invention may provide that the controller generates each stimulus via a signal 72 containing red, green, and blue image components associated therewith, and wherein one of these image components forms the video synchronization signal 74. In this embodiment a synchronization board receives the video synchronization signal 74, wherein the synchronization signal 72 from the controller forms an image with a visible synchronization element in the background of the frame as the synchronization indicia.

The synchronization of the video oculography based neuro-otologic testing and evaluation system according to invention is needed for accurate calculations based upon the eye data and the visual stimulus of small movements such as the measurement of micro-saccades; corrective saccades; pupil velocity; and pupil acceleration.

Saccade Reaction Time Testing Protocol

The present invention allows for easily adding motor reaction function and analysis function to saccade testing, and is collectively referenced herein as Saccade Reaction Time Testing.

Figure 11:
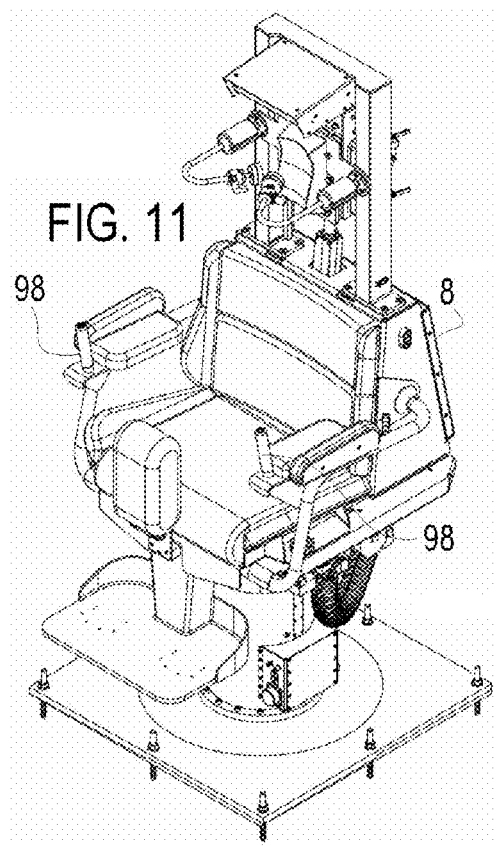
FIG. 11 illustrates an input device in the form of a rotary chair for performing a saccade reaction time testing protocol according to one embodiment of the present invention.

In a conventional saccade testing a subject 5 is told to look at stimulus when it appears. Visual stimulus is presented in a position on display 22 requiring saccade movement of eye. This conventional testing provides a variety of relevant biomarkers for researchers and clinicians to review including eye movement peak velocity (i.e. a measure of eye movement from a static position to secondary saccade position/time), saccadic accuracy (which is a measure of the actual target or stimulus amplitude/saccadic amplitude), saccadic latency (time between stimulus and start of saccadic movement), and additional parameters associated with secondary or corrective saccade movements which generally require higher speed of the VOG such as 150 or 200 hz or higher. These parameters are described in U.S. Patent Publication 2012-0081666 which is incorporated herein by reference In saccade reaction time testing of the present invention the subject or subject has left and right input buttons 98 as shown in rotary chair 8 of FIG. 11. The subject 5 is presented with a standard saccade test via the display 22 and if saccade stimulus moves to right from the original origin or fixation target the subject 5 pushes the right button 98 and if it moves to the left the subject pushes the left button 98. The inputs from buttons 98 are directed to the controller 70 and this testing protocol adds motor reaction function and analysis function. Test adds parameters of motor function including latency (time till pushing button) and accuracy of direction (did subject press right button?).

FIGS. 12A-F illustrates display results and control parameters 100 associated with the saccade reaction time testing protocol according to one embodiment of the present invention.

Further the two buttons 98 could be unrelated to the inherent direction to increase mental function required in the testing protocol. For example, in increasing level of difficulty, the left and right buttons 98 may relate to up and down rather than left and right and the stimulus presented above or below a baseline or point. The left and right buttons 98 may be related to Blue stimulus images and Red stimulus images, respectively, which are selectively shown as the saccadic visual target. The buttons 98 may be related to an image of elephant and house image, respectively, which are selectively shown as the saccadic visual target. The Left and Right buttons 98 may be associated with other mental functions such as identifying a Noun or Verb text that is used as the saccadic stimulus, or identifying an Even or Odd number that is used as the saccadic stimulus or image.

The saccadic reaction time testing and the resulting parameters 100 can provide an important tool to address neurologic function in subjects and possibly diagnosis damage.

Video Oculography Monitoring Both Eye Saccade Testing with Stimulus in Only One Eye As noted above High speed Video Oculography allows for measuring response in both eyes while stimulating only a single eye. Essentially the non stimulated eye is occluded, but VOG systems 10 can obtain eye responses from such non stimulated eye during this testing. The present invention provides monitoring eye response relative to each other as only a single eye is stimulated and a comparison of the responses such as a ratio of values and/or a difference of values represents a significant biomarker and indicator of area of damage of neural network. This stimulation of one eye only while measuring the response of both eyes is not limited to Pupillometry and is useful in other areas including saccadic testing and saccadic reaction time testing in the present invention Independent and Comparative Analysis of Eyes for Gaze Testing or Independent Spontaneous Nystagmus Testing As noted above High speed Video Oculography allows for measuring response in both eyes, whether one or the other is stimulated or not. Gaze testing has been known, also called independent spontaneous nystagmus testing, in which a subject stares at imaginary target in dark (to avoid other stimulus) and eye drift is observed. The target 32 position may be identified with a lighted dot, which is removed. The present invention allows for this testing to be performed and for the system 10 to quantify the amount of drift of the left and right eyes 7 independently with such quantification including direction, magnitude, velocity and acceleration of drift. Further the present invention provides for a comparison of each parameter between the left and the right eye 7. The comparison parameters may be either (1) the difference between the two, i.e. the value of the left eye minus the value of the right eye for each parameter (or vice versa), or (2) the ratio between the two, i.e. the value of the left eye divided by the value of the right eye for each parameter (or the inverse). As discussed above the comparison parameters are believed to be particularly useful bio-indicators of neural damage.

Objective Antisaccade Test Response in VOG Environment

The present invention provides an objective Anti-Saccadic testing response in a VOG environment. The Anti-Saccade test protocol is to run a saccadic type test from a stimulus standpoint but the subject 5 is instructed to focus on a location that is in the opposite direction from the starting point or origin of the test as the target stimulus and that is the same distance. For example if the target image or stimulus appears about six inches to the right of the origin or base then the subject 5 is to focus on a spot about six inches to the left of the base. The anti-saccade testing introduces cognitive function and suppression characteristics to the testing protocol. Anti-Saccade testing response in VOG environment provides objective measurements of eye response, generally analogous to the saccade responses discussed above, including eye movement peak velocity (i.e. a measure of eye movement from a static position to secondary "anti-saccade" position/time), "anti-saccadic accuracy" (which is a measure of the actual target or stimulus amplitude/anti saccadic amplitude), anti-saccadic latency (time between stimulus and start of saccadic movement or anti-saccadic movement), and additional parameters associated with secondary or corrective saccade movements. Additionally, the eye movement response may break out initial non-suppressed movements toward the saccadic image as "unsuppressed" eye movement and begin the anti-saccade measurement calculations at the point when the subject begins to move to the "anti-saccade position."

Further the present invention provides a comparison of anti-saccade movement parameters for each eye and includes the stimulation of one eye only while measuring the response of both eyes in this anti-saccadic testing testing in the present invention.

Figures 13A, 13B:
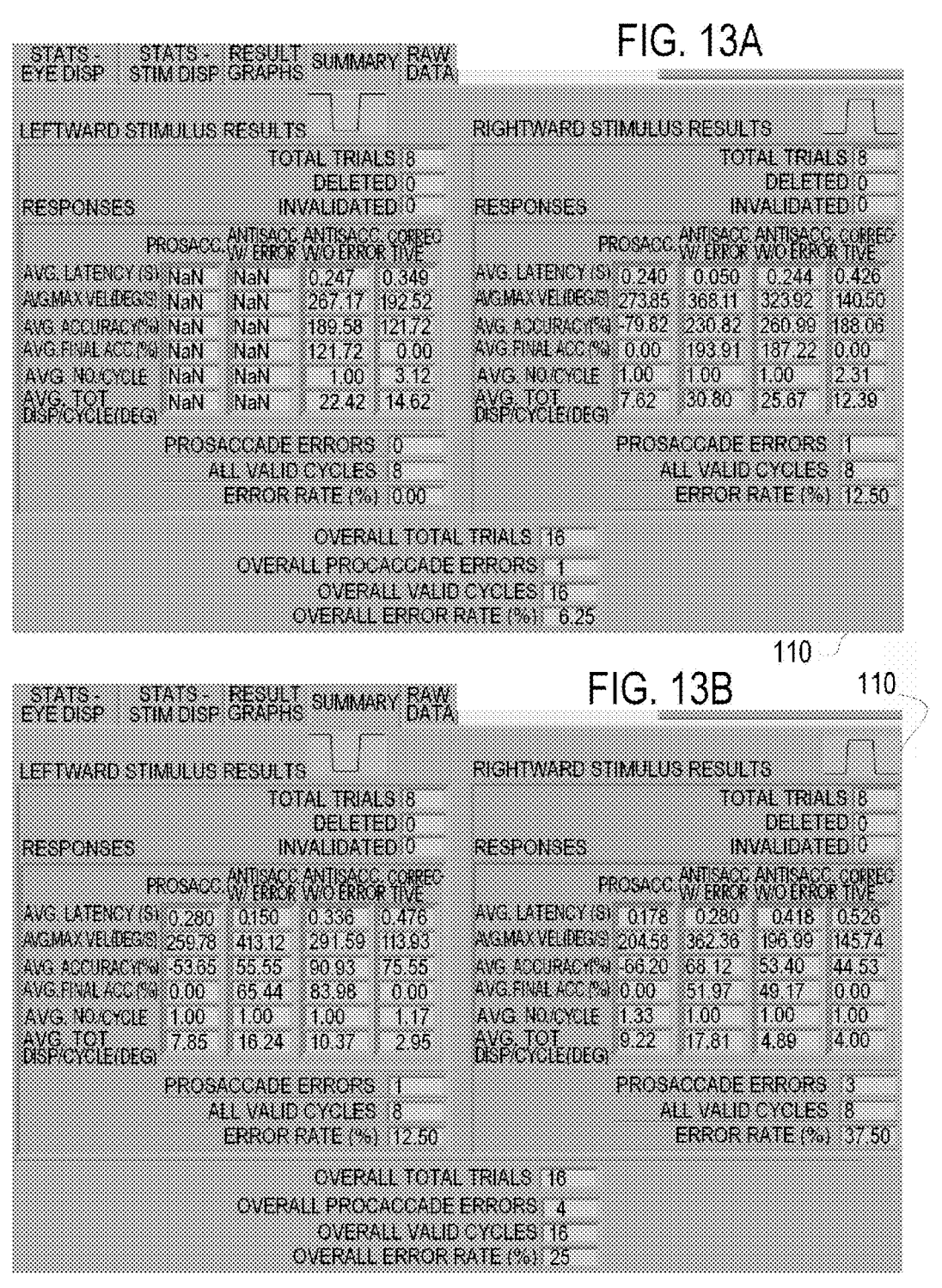

The parameters of interest include Anti-saccade peak eye velocity (separately for left and right eye); Anti-saccade latency (separately for left and right eye); Anti-saccade accuracy (separately for left and right eye); Anti-saccade overall accuracy (separately for left and right eye); Pro-saccade error (measure of error toward stimulus); and Absolute position error FIGS. 13A-B illustrate display results and control parameters, generally 110, associated with an objective anti-saccade test response testing protocol according to one embodiment of the present invention. FIG. 13 A illustrates the representative results of this testing on a subject 5 while FIG. 13B illustrates a representative error rate for the subject 5 in the testing protocol.

Predictive Saccade Testing Protocol in VOG Environment

Saccadic testing in a VOG environment is discussed in general above. In general the saccade testing utilizes random stimulus position (often along a defined axis, most often horizontal, sometimes vertical, possibly oblique). The present invention provides a test using the saccadic protocol except that the saccadic images will repeat in position after a given period of time, or more precisely after a given number of images, generally between 2 and 10, and more likely between 2 and 5 images. The parameters obtained in this predictive saccade testing include all of those discussed above in connection with saccadic testing.

Additionally the present invention will differentiate the results with each cycle. The main parameter of interest in the predictive saccade is the latency parameter, and how this changes with each cycle. The dwell time of each stimulus or image is also important for this test. This test results in a new biomarker or physiologic parameter, namely a measure of the number of cycles to predict each stimulus. This parameter is equal to the number of times until the latency parameter for a given stimulus is "less than" the stimulus origination time meaning the subject is predicting or anticipating the stimulus position. Varying the number of images and dwell time of each image is expected to vary the results for each subject. The system will also calculate the latency of responsive saccades that occurs after the pattern begins and also after the first predictive saccade.

As with the above, comparing the eye response together both when both eyes are stimulated and when one eye is occluded is included in the parameters maintained in the invention. FIGS. 14A-D illustrate display results and control parameters, generally 120, associated with Predictive saccade response testing protocol according to one embodiment of the present invention. It is believed a subject will have a personal pattern of predictive VS responsive that will preserver in post concussion but will have differing latencies.

% Of Saccade Function of a Smooth Pursuit Test as Indicator for MTBI

Figure 15:
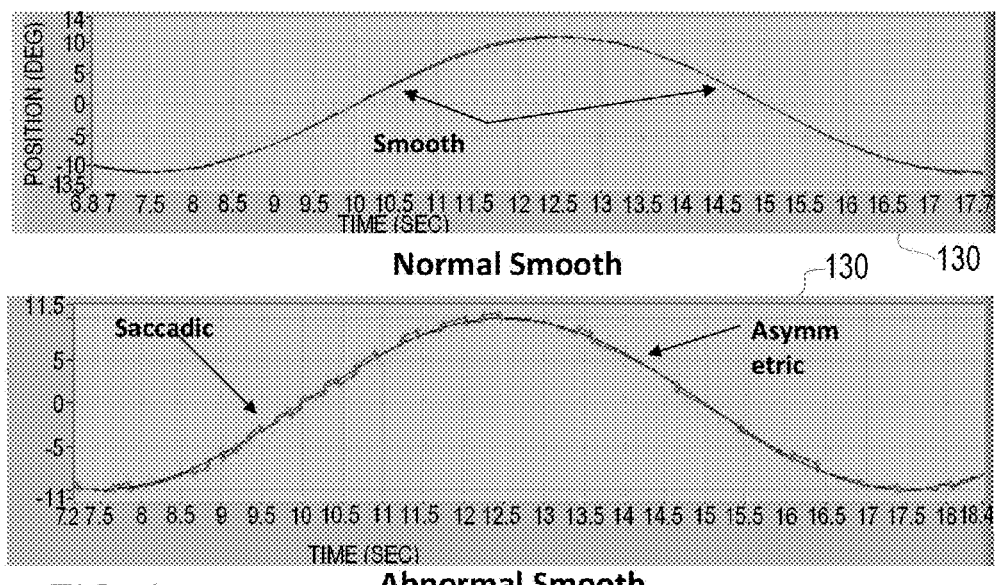
FIG. 15 illustrates display results and control parameters associated with a normal and abnormal response in a percent of saccade function of a smooth pursuit testing protocol which may be utilized as an indicator for mTBI according to one embodiment of the present invention.
Figure 16A:
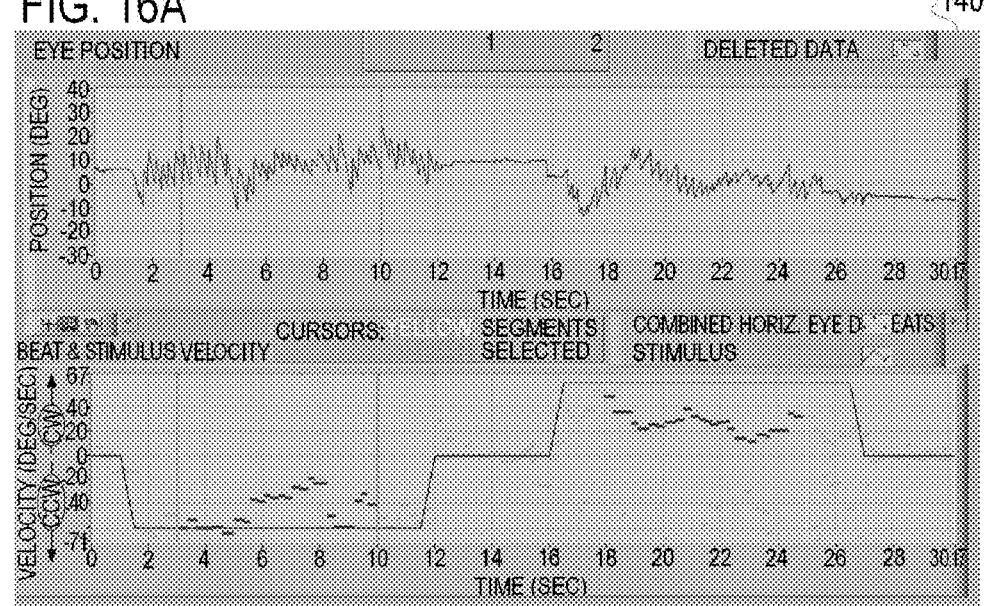
FIGS. 16A-D illustrate display results and control parameters associated with video oculographic quantification of the fast phase optokinetic stimulated nystagmus testing protocol according to one embodiment of the present invention.
Figures 16B, 16C, 16D:
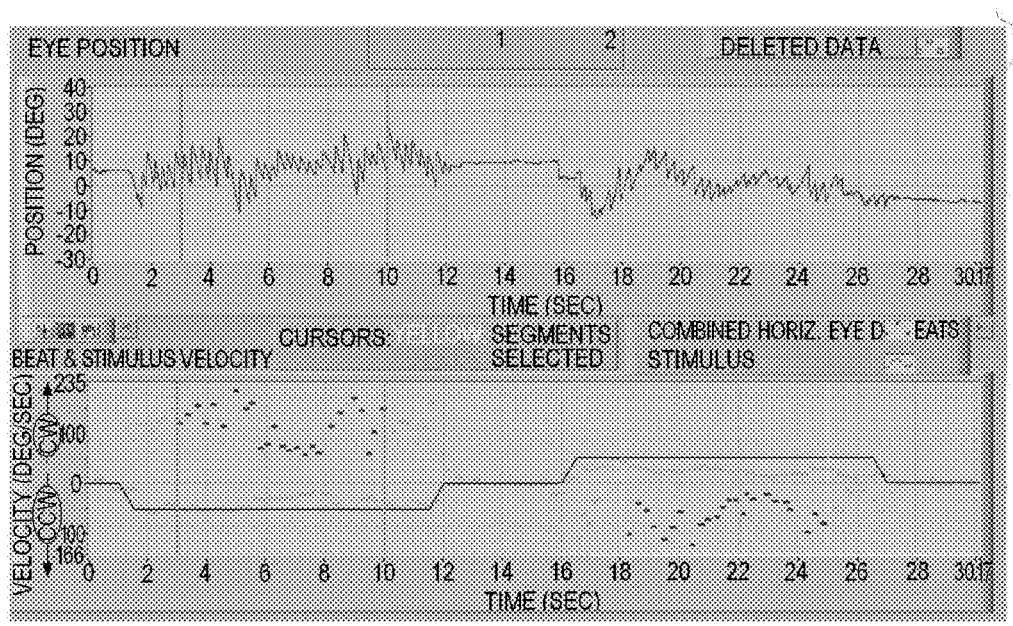

The present invention provides for a calculation of % of saccade function of a smooth pursuit test as indicator for mTBI, initiation time also a critical factor for mTBI, slow and fast target speeds helpful in mTBI diagnostic, such as 0.1 hz (6.2 degrees/second) and 1 hz (62 degrees/second) rior art is out there for general presentation of % of saccade function. FIG. 15 illustrates display results and control parameters, generally 130, associated with a normal and abnormal response in a percent of saccade function of a smooth pursuit testing protocol which may be utilized as an indicator for mTBI according to one embodiment of the present invention.

Video Oculographic Quantification of the Fast Phase Optokinetic Stimulated Nystagmus in Healthy Subjects One aspect of the present invention includes providing an effective tool to analyze the relation between amplitude and the fast phase peak velocity (FPV) and intra and inter individual variability of optokinetic generated nystagmus (OKN) for healthy individuals (normals), and to evaluate the clinical utility of such normative data to permit identification of statistically significant differences between controls and subjects who have had a recent concussion (mTBI).

The stimulus in such a test may be an alternating black and white vertical striped pattern moving clockwise (CW) and counterclockwise (CCW) in the yaw plane at 20 deg/sec. (d/s) and 60 d/s in an immersive environment: 90% or more of the visual field, in a "stare" mode. Peak fast phase velocity shall be recorded with each subject tested in two distinct sessions with a video-oculography (VOG) "bright-pupil" system connected by "fire-wire" to a computer and sampled at a rate of 100 Hz.

As early as the 1970s, the study of SPV in the animal model resulted in a quantitative analysis of its velocity characteristics. An electrooculography montage (EOG) recorded eye movements which were differentiated by amplifiers with a 3 msec. time constant and rectified to get the slow phase velocity without mention of the system sample rate. (Cohen, 1977) By the 1980s, the focus had broadened to evaluation of the clinical utility of assessing FPV, both peak and symmetry, in subjects with central pathology as compared to a normal control group N=20. Subjects were in an immersive environment with EOG capture with a sample rate of 200/sec. The velocity was reduced significantly in subjects with unilateral lesions in thalamus, midbrain and pons and that for these regions as well as the medulla and cerebellum there was a direction asymmetry of velocity which was level dependent. The authors concluded that the quantitative evaluation of velocity may offer, "important information on the mapping of lesions in patients with CNS disorders." (Kanayama, Kato, Nakamura, & Koike, 1987).

Chiba reported in 1989 the largest control group N=834 with an age range of 11 to 82 that evaluated a parameter of FPV: mean eye velocity. EOG recorded eye movements: the amplifier time constant, degree of immersive environment and sample rate were not included. He found no significant difference in average or normal deviation in subjects ages 11-49. In the next decade, the utility of such analysis was supported by data which identified below normal FPV, defined as two standard deviations from Chiba's norms, as characteristic of pontine level lesions. (Yamada, 1991). Commercial video eye tracking systems: video-oculography (VOG) became available in North America in the mid-1980s and by the end of the first decade of the twenty-first century had been, "adopted by several manufacturers of vestibular testing equipment due to their reliability, precision, patient comfort and ease of use." (Jacobson Gary P. & McCaslin Devin L., 2008)

This invention provides a tool a comprehensive analysis of multiple parameters of FPV as recorded with VOG to establish normative data as the literature is not replete with such reports. The effort to establish such norms, to provide a standard against which a subject population may be measured, appears justified in that previous researchers, albeit employing a limited FPV analysis with EOG, found it a useful tool to evaluate central function. The present invention provides an effective biomarker in the ratio of the velocity of the fast phase of nystagmus to the velocity of slow phase of nystagmus generated by immersive optokinetic stimulation and uses this biomarker as an indication of central oculomotor function in human subjects.

The parameters reviewed include Average slow phase velocity and asymmetry for slow phase Average fast phase velocity and asymmetry for fast phase and following is a representative slow phase eye velocity response. FIGS. 16A-D illustrate display results and control parameters, generally 140, associated with video oculographic quantification of the fast phase optokinetic stimulated nystagmus testing protocol according to one embodiment of the present invention.

CONCLUSION

The present invention provides tools for clinicians, researchers, and caregivers that can be used in a number of distinct applications. For example consider eye tracking of younger and elderly people in association with the task of walking. Elderly subjects depend more on foveal vision than younger subjects during walking. Their walking speed is decreased by a limited visual field, probably caused by a deteriorated peripheral vision. Younger subjects make use of both their central and peripheral vision while walking. Their peripheral vision allows faster control over the process of walking. The present method and apparatus provides tool to better explore and remediate these issues.

Although the present invention has been described with particularity herein, the scope of the present invention is not limited to the specific embodiment disclosed. It will be apparent to those of ordinary skill in the art that various modifications may be made to the present invention without departing from the spirit and scope thereof. The scope of the invention is not to be limited by the illustrative examples described above.

What is claimed is:

1. A video oculography based neuro-otologic testing and evaluation system comprising:
    A base adapted to be positioned adjacent to a subject's head;
    At least one digital camera attached to the base, operating at least at 60 frames per second and configured to take images of at least one of the subject's eyes;
    A display for selectively displaying visual stimulus to the subject;
    A controller coupled to the display generating each visual stimulus to be displayed and coupled to each digital camera and receiving and storing data signals there from, the controller configured to calculate eye related data from the digital camera images, and configured to display the eye related data to users;
    A video synchronization signal generated by the controller associated with each visual stimulus which identifies when the display is displaying the associated visual stimulus to the subject;
    Receiving and coupling the video synchronization signal with at least the eye data from the digital camera, wherein the received video synchronization signal and the eye data from the digital camera are utilized by the controller to synchronize calculations based upon the eye data and the visual stimulus.

2. The video oculography based neuro-otologic testing and evaluation system according to claim 1 further including a photodiode coupled to the display screen, wherein the photodiode receives the video synchronization signal from the display.

3. The video oculography based neuro-otologic testing and evaluation system according to claim 2 wherein the controller creates the video synchronization signals as synchronization pulses of video display elements of the display which are received by the photodiode.

4. The video oculography based neuro-otologic testing and evaluation system according to claim 2 wherein the photodiode signals associated with the video synchronization signals is paired to the eye data via an input on the digital cameras.

5. The video oculography based neuro-otologic testing and evaluation system according to claim 2 wherein the controller uses data from the photodiode to calibrate the brightness of the display.

6. The video oculography based neuro-otologic testing and evaluation system according to claim 1 wherein the controller generating each stimulus generates a stimulus signal containing red, green, and blue image components associated therewith, and wherein one of these image components forms the video synchronization signal.

7. The video oculography based neuro-otologic testing and evaluation system according to claim 6 further including a synchronization board receiving the video synchronization signal, wherein the video synchronization signal corresponds to an image with a visible synchronization element in the background of the frame as the synchronization indicia.

8. The video oculography based neuro-otologic testing and evaluation system according to claim 7 wherein the synchronization signal is paired with the eye images and returned to the controller for analysis.

9. The video oculography based neuro-otologic testing and evaluation system according to claim 1 wherein calculations based upon the eye data and the visual stimulus include measurement of at least one of micro-saccades; corrective saccades; pupil velocity; and pupil acceleration.

10. The video oculography based neuro-otologic testing and evaluation system according to claim 9 wherein the base is a head mounted google and the display is mounted on the goggles.

11. A video oculography based neuro-otologic testing and evaluation method comprising the steps of:
    Obtaining images of at least one of the subject's eyes at least at 60 frames per second with at least one digital camera attached to a base positioned adjacent to a subject's head;
    Selectively displaying visual stimulus to the subject on a display visible to the subject;
    Generating each visual stimulus to be displayed from a controller coupled to the display;
    Receiving and storing data signals from each digital camera in the controller;
    Calculating eye related data from the digital camera images and the visual stimulus;
    Displaying the eye related data to users;
    Generating a video synchronization signal by the controller associated with each visual stimulus which identifies when the display is displaying the associated visual stimulus to the subject;
    Receiving and coupling the video synchronization signal with at least the eye data from the digital camera; and Synchronizing calculations based upon the eye data and the visual stimulus by the controller based upon the received video synchronization signal and the eye data from the digital camera.

12. The video oculography based neuro-otologic testing and evaluation method according to claim 11 further including a photodiode coupled to the display screen, wherein the photodiode receives the video synchronization signal from the display.

13. The video oculography based neuro-otologic testing and evaluation method according to claim 12 wherein the controller creates the video synchronization signals as synchronization pulses of video display elements of the display which are received by the photodiode.

14. The video oculography based neuro-otologic testing and evaluation method according to claim 12 wherein the photodiode signals associated with the video synchronization signals is paired to the eye data via an input on the digital cameras.

15. The video oculography based neuro-otologic testing and evaluation method according to claim 12 wherein the controller uses data from the photodiode to calibrate the brightness of the display.

16. The video oculography based neuro-otologic testing and evaluation method according to claim 11 wherein the controller generating each stimulus generates a stimulus signal containing red, green, and blue image components associated therewith, and wherein one of these image components forms the video synchronization signal.

17. The video oculography based neuro-otologic testing and evaluation method according to claim 16 further including a synchronization board receiving the video synchronization signal, wherein the synchronization signal corresponds to an image with a visible synchronization element in the background of the frame as the synchronization indicia.

18. The video oculography based neuro-otologic testing and evaluation method according to claim 17 wherein the synchronization signal is paired with the eye images and returned to the controller for analysis.

19. The video oculography based neuro-otologic testing and evaluation method according to claim 11 wherein calculations based upon the eye data and the visual stimulus include measurement of at least one of micro-saccades; corrective saccades; pupil velocity; and pupil acceleration.

20. The video oculography based neuro-otologic testing and evaluation method according to claim 19 wherein the base is a head mounted google and the display is mounted on the goggles.

* * * * *